US011351185B2

(12) United States Patent
Jiang et al.

(10) Patent No.: US 11,351,185 B2
(45) Date of Patent: Jun. 7, 2022

(54) USE OF ISOVALERYLSPIRAMYCINS AS ANTI-CANCER AGENTS TO INHIBIT METASTASIS

(71) Applicants: ASCLEA CORPORATION, Las Vegas, NV (US); THE UNITED STATES OF AMERICA, as represented by the Secretary, Dept. of Health and Human Svcs., Bethesda, MD (US)

(72) Inventors: Enhong Jiang, Liaoning (CN); Zhengping Zhuang, Bethesda, MD (US); Jing Cui, Potomac, MD (US)

(73) Assignees: ASCLEA CORPORATION, Las Vegas, NV (US); THE UNITED STATES OF AMERICA, AS REPRESENTED BY THE SECRETARY, DEPARTMENT OF HEALTH AND HUMAN SERVICES OFFICE OF TECHNOLOGY TRANSFER, NATIONAL INSTITUTES OF HEALTH, Bethesda, MD (US)

(*) Notice: Subject to any disclaimer, the term of this patent is extended or adjusted under 35 U.S.C. 154(b) by 0 days.

(21) Appl. No.: 16/816,068

(22) Filed: Mar. 11, 2020

(65) Prior Publication Data

US 2021/0283159 A1    Sep. 16, 2021

(51) Int. Cl.
*A61K 31/7048* (2006.01)
*A61P 35/04* (2006.01)

(52) U.S. Cl.
CPC .......... *A61K 31/7048* (2013.01); *A61P 35/04* (2018.01)

(58) Field of Classification Search
None
See application file for complete search history.

(56) References Cited

U.S. PATENT DOCUMENTS

| | | | |
|---|---|---|---|
| 8,778,896 B2 | 7/2014 | Jiang et al. | |
| 2019/0350908 A1 | 11/2019 | Christiano | |
| 2020/0030351 A1 | 1/2020 | Jiang et al. | |
| 2020/0163984 A1 | 5/2020 | Jiang et al. | |
| 2020/0405739 A1* | 12/2020 | Xia | A61P 35/02 |

FOREIGN PATENT DOCUMENTS

| | | |
|---|---|---|
| CN | 1174238 A | 2/1998 |
| CN | 101054553 A | 10/2007 |
| CN | 101785778 A | 7/2010 |
| EP | 3 607 952 A1 | 2/2020 |
| EP | 3 639 829 A1 | 4/2020 |
| EP | 3741374 A1 | 11/2020 |
| WO | 2007/144876 A1 | 12/2007 |
| WO | 2018/184587 A1 | 10/2018 |
| WO | 2019/007368 A1 | 1/2019 |
| WO | 2019/141254 A1 | 7/2019 |
| WO | 2021/068910 A1 | 4/2021 |

OTHER PUBLICATIONS

Montanaro, AJP Aug. 2008, vol. 173, No. 2, pp. 301-310. (Year: 2008).*
Kang, J Oncol. 2019; 2019: 8676947, pp. 1-2. (Year: 2019).*
Gaviraghi, Cells 2019, 8, 1098, pp. 1-16. (Year: 2019).*
Ashy et al., "Carbomycin, a Macrolide Antibiotic", Department of Chemistry, Faculty of Science, vol. 135, 1980, pp. 541-551.
Bernstein et al., "DNA Damage, DNA Repair and Cancer", Chapter 16, May 22, 2013, pp. 413-466.
Carlson et al., "Targeting the Perivascular Niche Sensitizes Disseminated Tumour Cells to Chemotherapy", Nature Cell Biology, vol. 21, No. 2, Feb. 2019, pp. 238-250.
Cheng et al., "Genome Maintenance by Selenoprotein H in the Nucleolus (OR11-03-19)", Current Developments in Nutrition, vol. 3, Suppl. 1, Jun. 13, 2019, 1 page.
Chenghang et al., "Isolation and Structure Determination of Shengjimycin E ( 4"-isovalerylspiramycin I )", Chinese Journal of Antibiotics, vol. 25, No. 1, 2000, pp. 1-5.
Chenghang et al., "Shengjimycins: a Group of Hybrid Antibiotics, 4"-Acylspiramycins", Actinomycetologica, vol. 13, No. 2, Jun. 12, 1999, pp. 120-125.
Cooke et al., "Oxidative DNA Damage: Mechanisms, Mutation, and Disease", The FASEB Journal, vol. 17, Jul. 2003, pp. 1195-1214.
Cox et al., "Selenoprotein H is an Essential Regulator of Redox Homeostasis that Cooperates with P53 in Development and Tumorigenesis", Proceedings of the National Academy of Sciences, vol. 113, No. 38, Sep. 1, 2016, pp. E5562-E5571.
D'Almeida et al., "Encapsulated Mir-200c and Nkx2.1 in a Nuclear/Mitochondria Transcriptional Regulatory Network of Non-Metastatic and Metastatic Lung Cancer Cells", BMC Cancer, vol. 19, Article No. 136, 2019, pp. 1-24.
Derenzini et al., "What the Nucleolus Says to a Tumour Pathologist", Histopathology, vol. 54, 2009, pp. 753-762.
Epp et al., "Production of a Hybrid Macrolide Antibiotic in Streptomyces Ambofaciens and Streptomyces Lividans by Introduction of a Cloned Carbomycin Biosynthetic Gene from Streptomyces Thermotolerans", Gene, vol. 85, Dec. 28, 1989, pp. 293-301.
Frankowski et al., "Metarrestin, A Perinucleolar Compartment Inhibitor, Effectively Suppresses Metastasis", Science Translational Medicine, vol. 10, No. 441, May 16, 2018, pp. 1-30.
He et al., "Remodeling of Metastatic Vasculature Reduces Lung Colonization and Sensitizes Overt Metastases to Immunotherapy", Cell Reports, vol. 30, Jan. 21, 2020, pp. 714-724.

(Continued)

*Primary Examiner* — Layla D Berry
(74) *Attorney, Agent, or Firm* — Buchanan Ingersoll & Rooney PC

(57) ABSTRACT

A pharmaceutical composition containing any one or more of 4"-O-isovalerylspiramycin I, II and III counters tumorigenesis and reduces or prevents metastasis by inhibiting selenoprotein H to trigger genomic instability and cell-cycle arrest in cancer cells.

17 Claims, 13 Drawing Sheets

(56) References Cited

OTHER PUBLICATIONS

Hossain et al., "Membrane Extraction of a New Antibiotic (Shengjimycin): Equilibrium and Mass Transfer Analysis", Journal of Chemical Technology & Biotechnology, vol. 86, Aug. 19, 2011, pp. 1247-1255.
Jandial Rahul, "Metastatic Cancer Clinical and Biological Perspectives", CRC Press, Aug. 7, 2013, 1 page.
Janku et al., "Targeting the PI3K Pathway in Cancer: Are We Making Headway?", Nature Reviews Clinical Oncology, vol. 15, No. 5, May 2018, pp. 273-291.
Kofuji et al., "IMP Dehydrogenase-2 Drives Aberrant Nucleolar Activity and Promotes Tumorigenesis in Glioblastoma", Nature Cell Biology, vol. 21, No. 8, Aug. 1, 2019, pp. 1003-1014.
Li et al., "Effect of Branched-Chain Amino Acids, Valine, Isoleucine and Leucine on the Biosythesis of Bitespiramycin 4"-O-Acylspiramycins", Brazilian Journal of Microbiology, vol. 40, 2009, pp. 734-746.
Lu et al., "Engineering of Leucine-Responsive Regulatory Protein Improves Spiramycin and Bitespiramycin Biosynthesis", Microbial Cell Factories, vol. 18, Article No. 38, Feb. 19, 2019, pp. 1-12.
Ma et al., "Construction of 4"-Isovalerylspiramycin-1-Producing Strain by In Frame Partial Deletion of 3-0-Acyltransferase Gene in Streptomyces spiramyceticus WSJ-1, the Bitespiramycin Producer", Current Microbiology, vol. 62, 2011, pp. 16-20.
Mayer et al., "The Nucleolus as a Stress Sensor: JNK2 Inactivates the Transcription Factor TIF-IA and Down-Regulates Rrna Synthesis", Genes & Development, vol. 19, 2005, pp. 933-941.
Morita et al., "mTOR Controls Mitochondrial Dynamics and Cell Survival Via MTFP1", Molecular Cell, vol. 69, 2017, pp. 922-935.
Nair et al., "A Simple Practice Guide for Dose Conversion between Animals and Human", Journal of Basic and Clinical Pharmacy, vol. 7, No. 2, Mar.-May 2016, pp. 27-31.
Novoselov et al., "Selenoprotein H is a Nucleolar Thioredoxin-Like Protein with a Unique Expression Pattern", The Journal of Biological Chemistry, vol. 282, No. 16, Apr. 20, 2007, pp. 11960-11968.
Penzo et al., "The Ribosome Biogenesis—Cancer Connection", Cells, vol. 8, No. 1, Article No. 55, Jan. 15, 2019, pp. 1-15.
Santos-Pereira et al., "R loops: New Modulators of Genome Dynamics and Function", Nature Reviews Genetics, vol. 16, Oct. 2015, pp. 583-597.
Shang et al., "Construction and Physiological Studies on a Stable Bioengineered Strain of Shengjimycin", The Journal of Antibiotics, vol. 54, No. 1, Jan. 2001, pp. 66-73.
Shang et al., "Construction of a Stable Bioengineered Strain of Biotechmycin", Institute of Medicinal Biotechnology, CAMS & PUMC, vol. 15, No. 2, Apr. 1999, pp. 105-111.
Shi et al., "Acid Catalysed Degradation of Some Spiramycin Derivatives Found in the Antibiotic Bitespiramycin", Journal of Pharmaceutical and Biomedical Analysis, vol. 36, Nov. 15, 2004, pp. 593-600.
Shi et al., "Structural Identification of Bitespiramycin Metabolites in Rat: A Single Oral Dose Study", Xenobiotica, vol. 35, No. 4, Sep. 22, 2008, pp. 343-358.
Shi et al., "Tissue Distribution of Bitespiramycin and Spiramycin in Rats", Acta Pharmacologica Sinica, vol. 25, No. 11, Nov. 2004, pp. 1396-1401.
Short et al., "Selenoproteins in Tumorigenesis and Cancer Progression", Advances in Cancer Research, vol. 136, 2017, pp. 49-83.
Sun et al., "A New Model of Time Scheme for Progression of Colorectal Cancer", BMC Systems Biology, vol. 8, Suppl. 3, Oct. 22, 2014, pp. 1-8.
Teng et al., "ROS-Induced R Loops Trigger a Transcriptioncoupled but BRCA1/2-Independent Homologous Recombination Pathway Through CSB", Nature Communications, vol. 9, Article No. 4115, 2018, pp. 1-12.
Thorn et al., "Doxorubicin Pathways: Pharmacodynamics and Adverse Effects", Pharmacogenet Genomics, vol. 22, No. 7, Jul. 2011, pp. 440-446.
Topalian et al., "Neoadjuvant Checkpoint Blockade for Cancer Immunotherapy", Cancer Immunotherapy, vol. 367, Jan. 31, 2020, pp. 1-11.
Wang et al., "Regulation of Branched-Chain Amino Acid Catabolism: Glucose Limitation Enhances the Component of Isovalerylspiramycin for the Bitespiramycin Production", Bioprocess and Biosystems Engineering, vol. 33, 2010, pp. 257-265.
Yang et al., "A Redox Mechanism Underlying Nucleolar Stress Sensing by Nucleophosmin", Nature Communications, vol. 7, Article No. 13599, Nov. 25, 2016, pp. 1-16.
Zhang et al., "Expression of 4"-0-Isovaleryltransferase Gene from Streptomyces Thermotolerans in Streptomyces Lividans TK24", Chinese Journal of Biotechnology, vol. 30, No. 9, Sep. 25, 2014, pp. 1390-1400.
Shalem et al., "Genome-Scale CRISPR-Cas9 Knockout Screening in Human Cells", Science, Jan. 3, 2014, 343 (6166), 84-87, pp. 1-10.
Liu et al., "Targeting IDH1-Mutated Malignancies with NRF2 Blockade", JNCI J Natl Cancer Inst, 2019, vol. 111, No. 10, pp. 1033-1041.
Lomenick et al., "Target identification using drug affinity responsive target stability (DARTS)", Proc. Nat'l Acad. Sci., Dec. 22, 2009, vol. 106, No. 51, pp. 21984-21989.
International Search Report and Written Opinion of the International Searching Authority dated Jul. 14, 2021, by the European Patent Office in corresponding International Patent Application No. PCT/US2021/021831. (13 pages).

* cited by examiner

Figure 1A
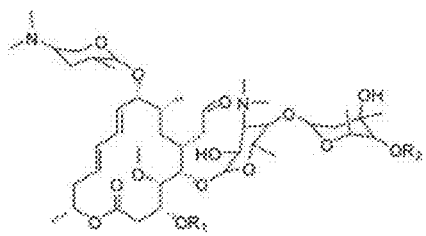
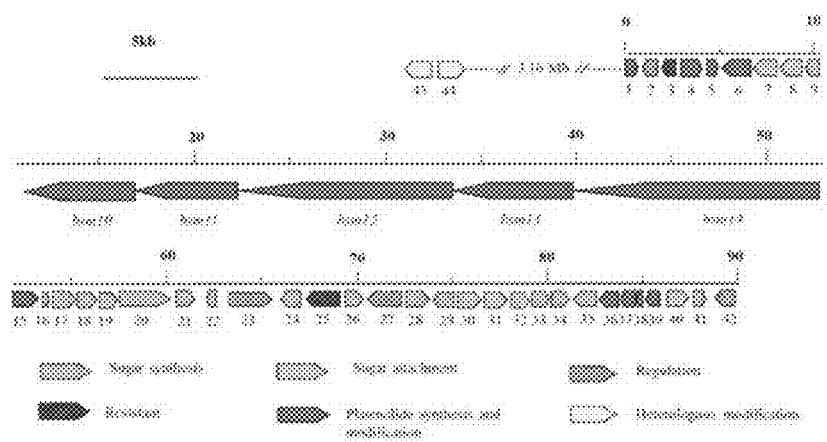
Figure 1B
Figure 1C
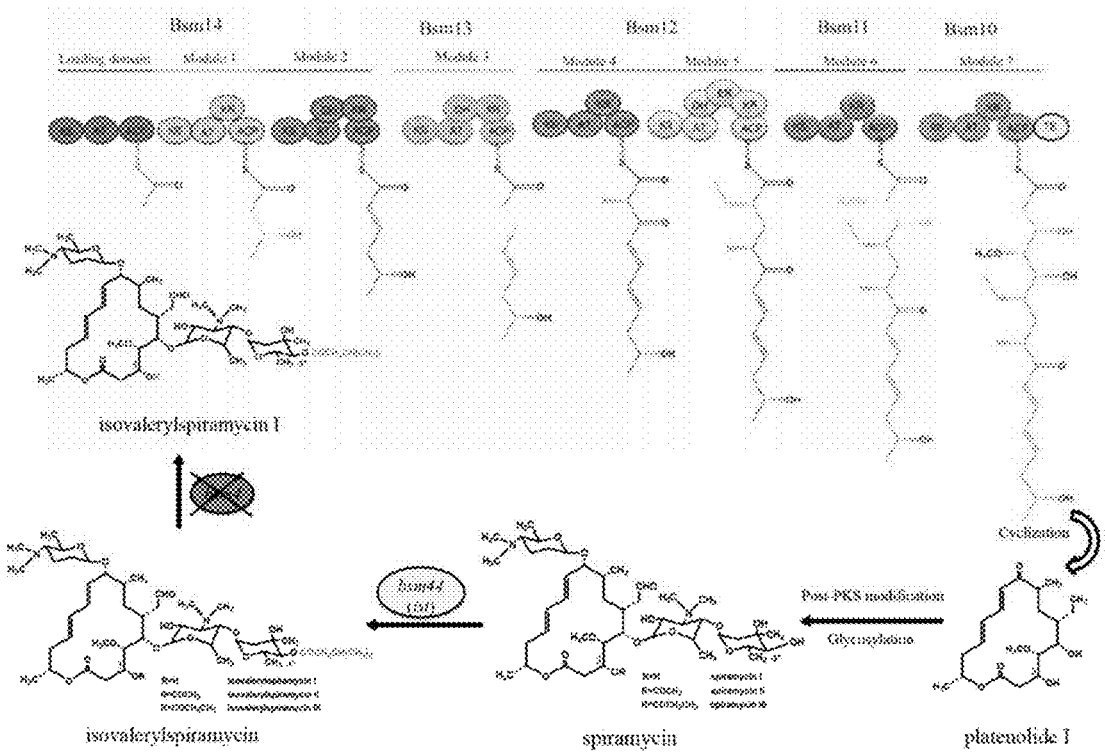

Figure 2A
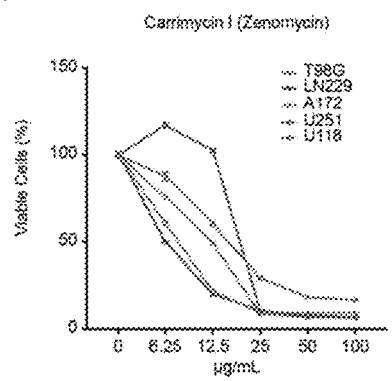
Figure 2B
| Cell line name | IC50 (µg/mL) |
|---|---|
| LN229 | 5.906 |
| A172 | 7.424 |
| T98G | 11.3 |
| U118 | 16.93 |
| U251 | 23.39 |
Figure 2C
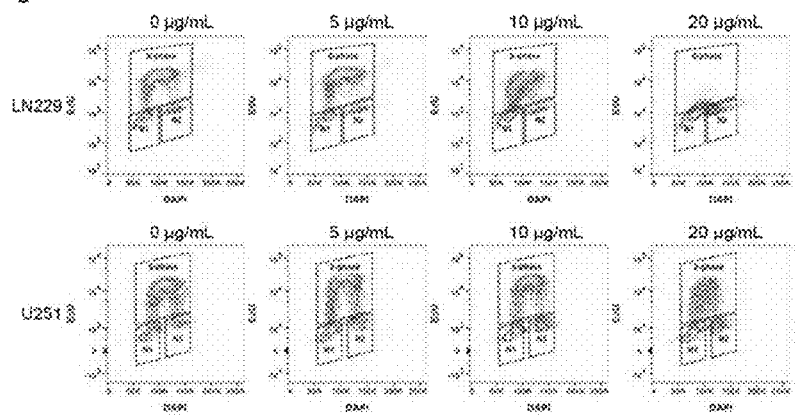
Figure 2D
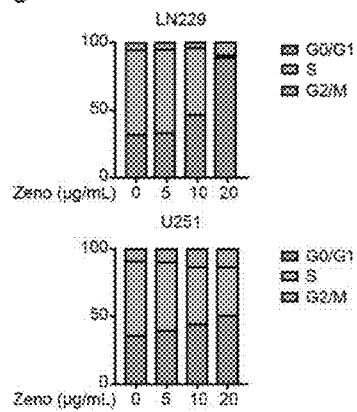
Figure 2E
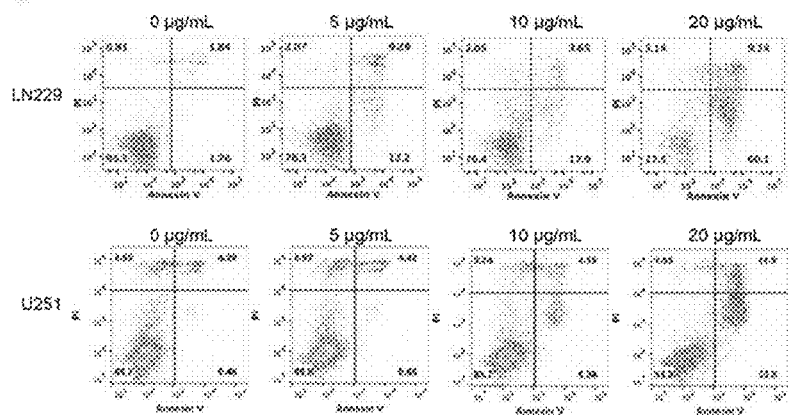
Figure 2F
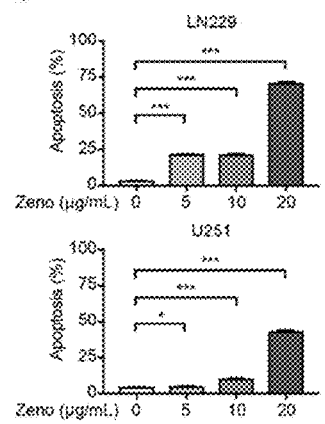

Figure 3A
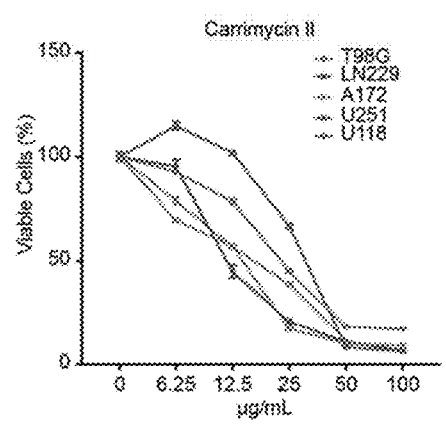
Figure 3B
| Cell line name | Carrimycin II IC50 (µg/mL) |
|---|---|
| LN229 | 13.06 |
| A172 | 12.17 |
| T98G | 15.79 |
| U118 | 23.92 |
| U251 | 29.21 |
Figure 3C
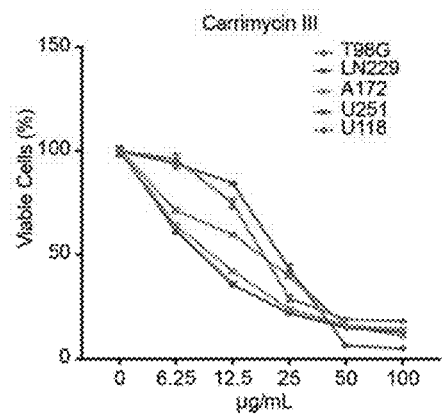
Figure 3D
| Cell line name | Carrimycin III IC50 (µg/mL) |
|---|---|
| LN229 | 8.457 |
| A172 | 9.801 |
| T98G | 15.75 |
| U118 | 19.90 |
| U251 | 22.50 |

Figure 4A
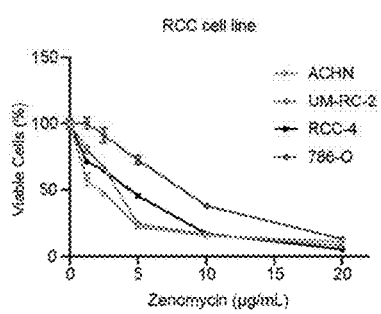
Figure 4B
| Cell line name | IC50 (µg/mL) |
|---|---|
| ACHN | 1.836 |
| UM-RC-2 | 3.212 |
| RCC4 | 3.549 |
| 786-O | 7.957 |
Figure 4C
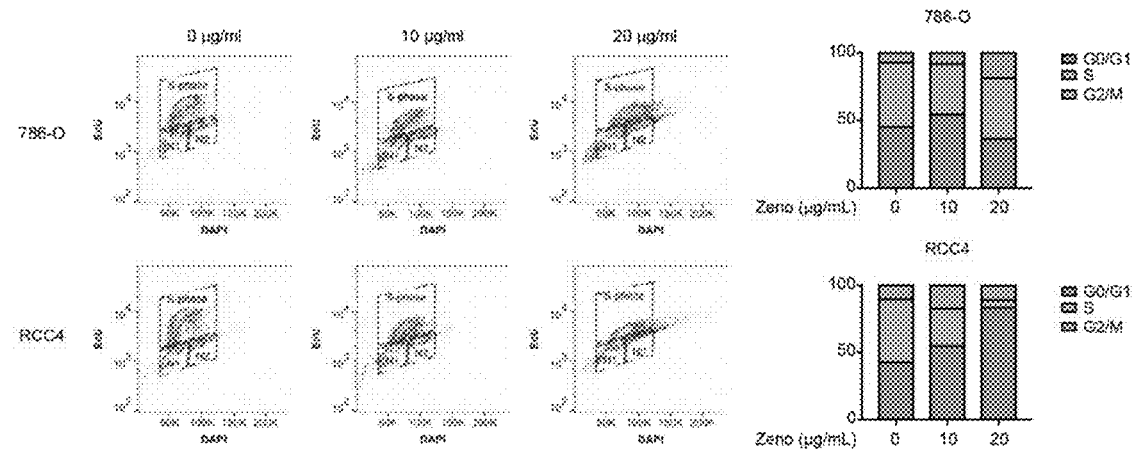
Figure 4D
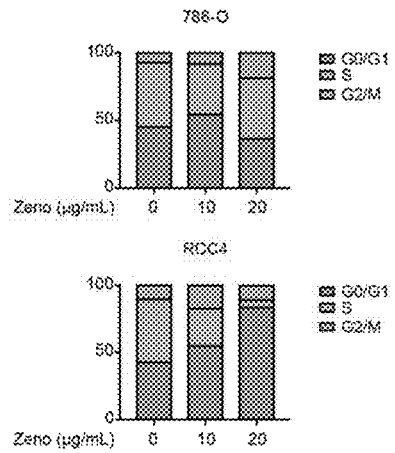
Figure 4E
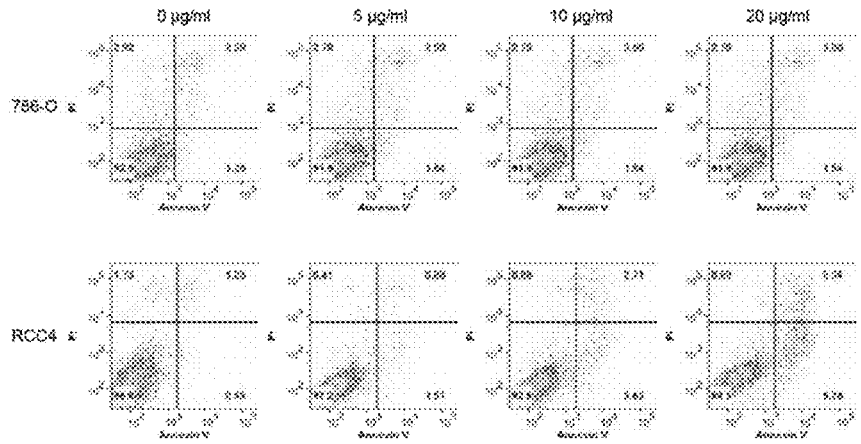
Figure 4F
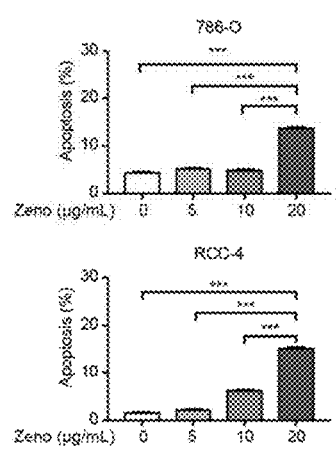

Figure 5A
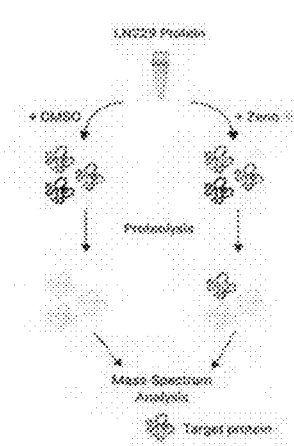
Figure 5B
Figure 5C
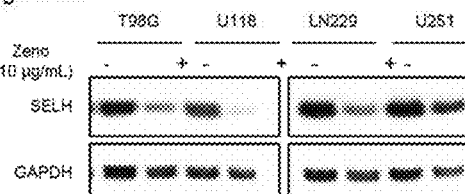
Figure 5D
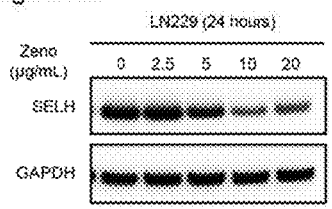
Figure 5E
Figure 5F
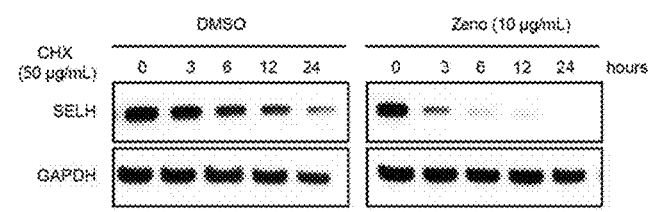
Figure 5G
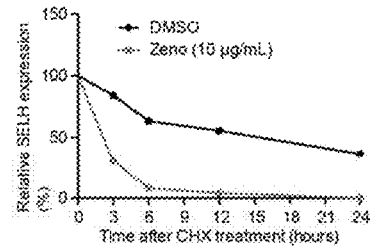
Figure 5H
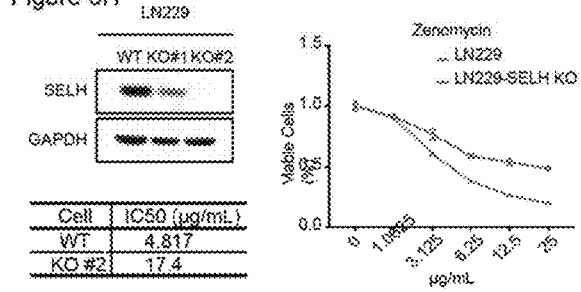
Figure 5I
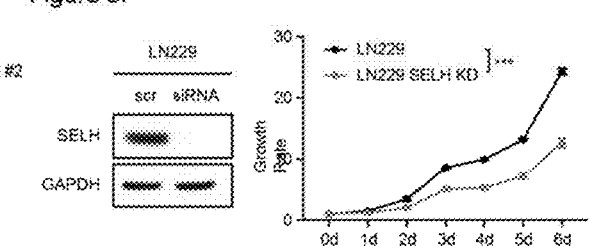
Figure 5J
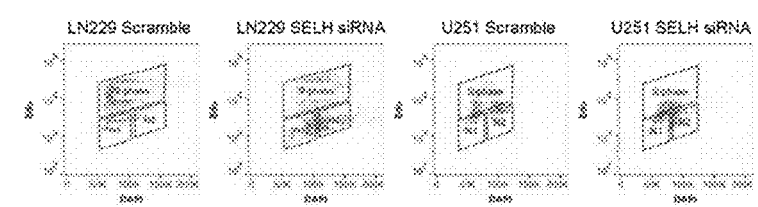
Figure 5K
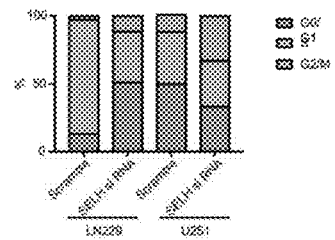
Figure 5L
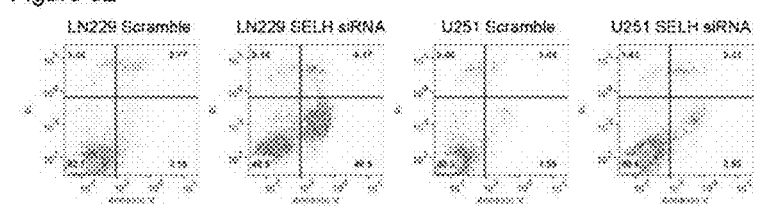
Figure 5M
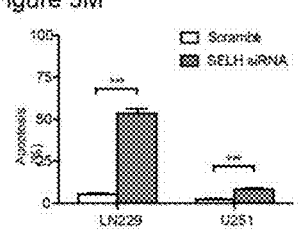

Figure 6A
Figure 6C
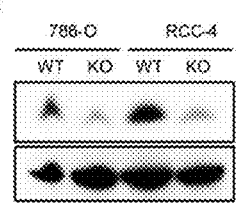
Figure 6B
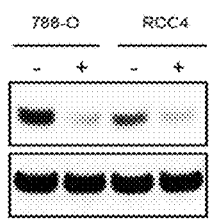
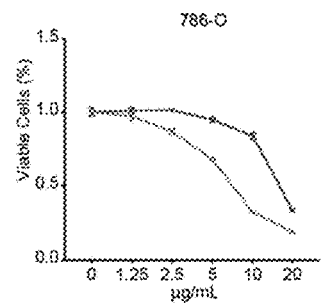
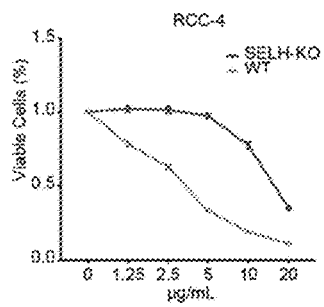
Figure 6D
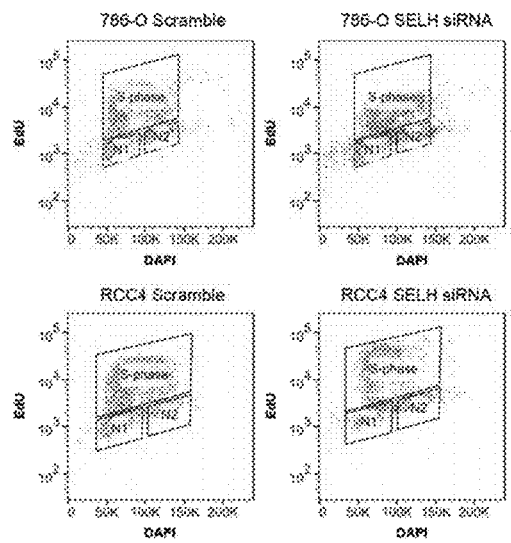
Figure 6E
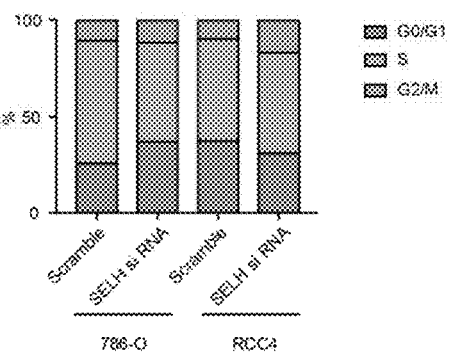
Figure 6F
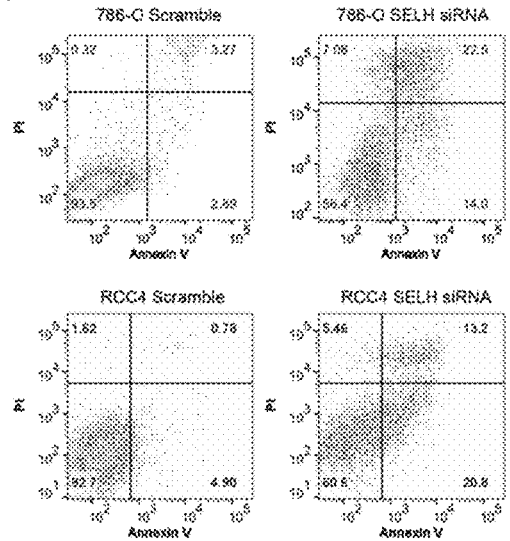
Figure 6G
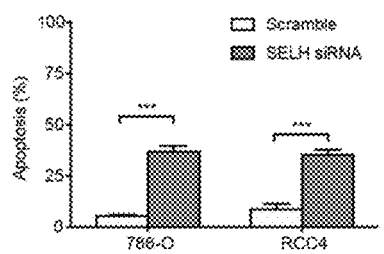

Figure 7A
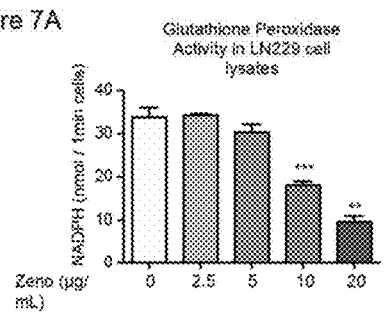
Figure 7B
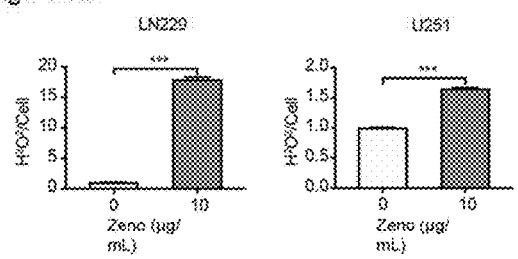
Figure 7C
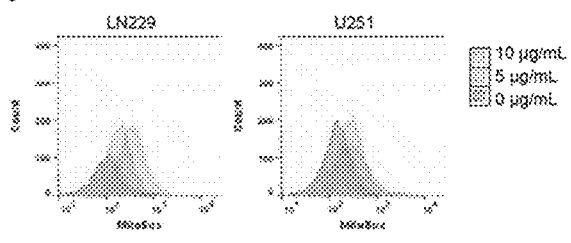
Figure 7D
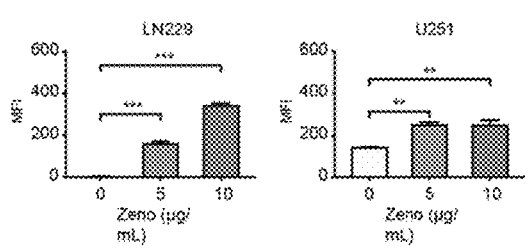
Figure 7E
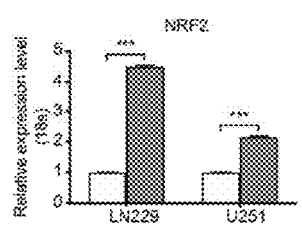
Figure 7F
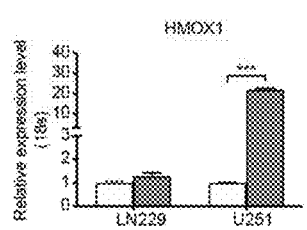
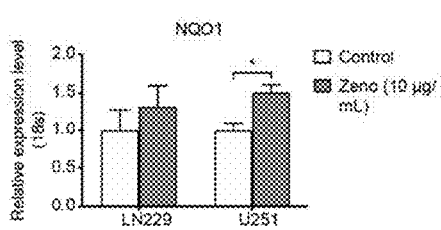
Figure 7G
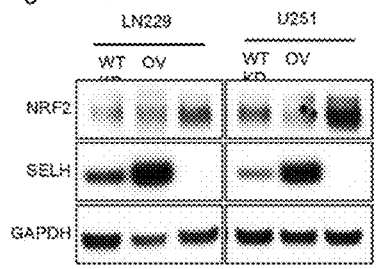
Figure 7H
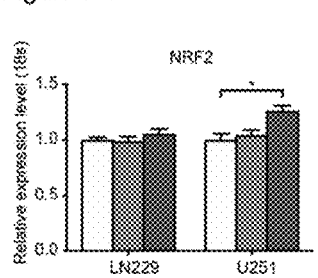
Figure 7I

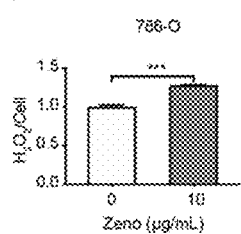
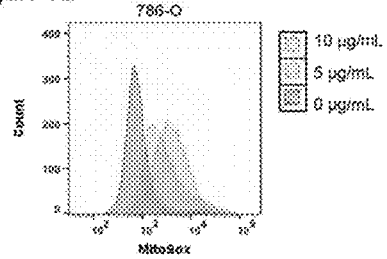
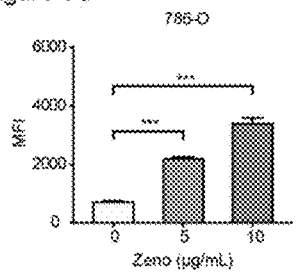
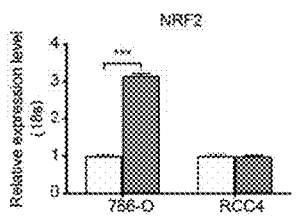
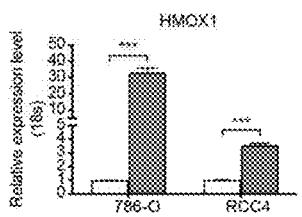
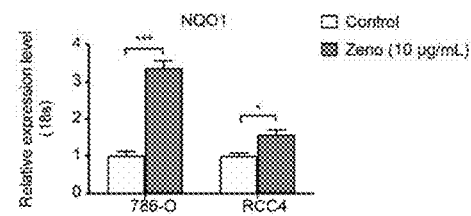
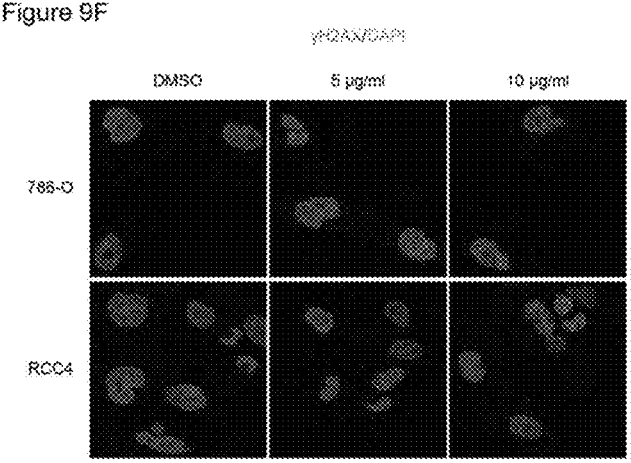
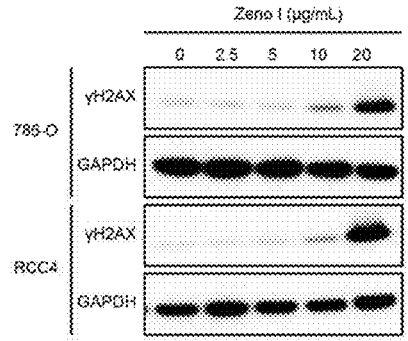

Figure 12A
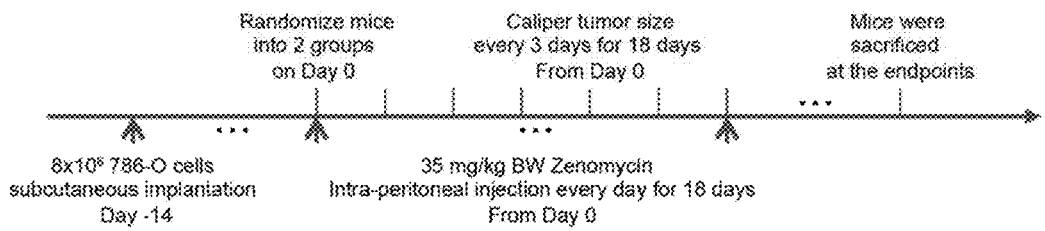
Figure 12B
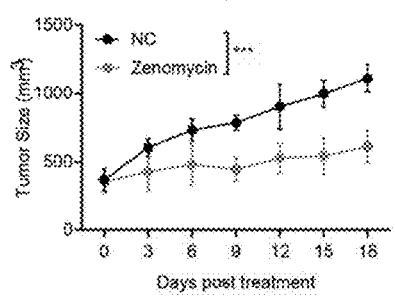
Figure 12C
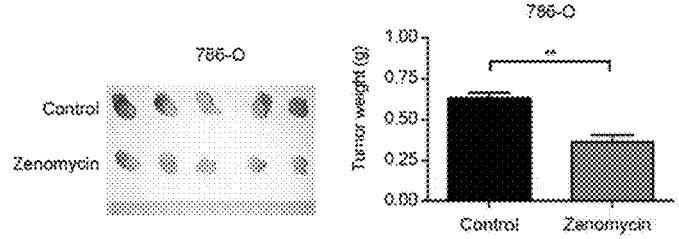
Figure 12D
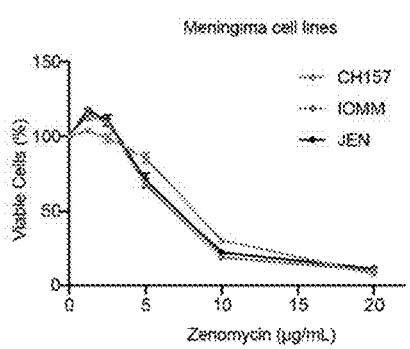
Figure 12E
| Cell line name | IC50 (µg/mL) |
| --- | --- |
| IOMM | 9.724 |
| JEN | 10.30 |
| CH-157 | 12.11 |
Figure 12F
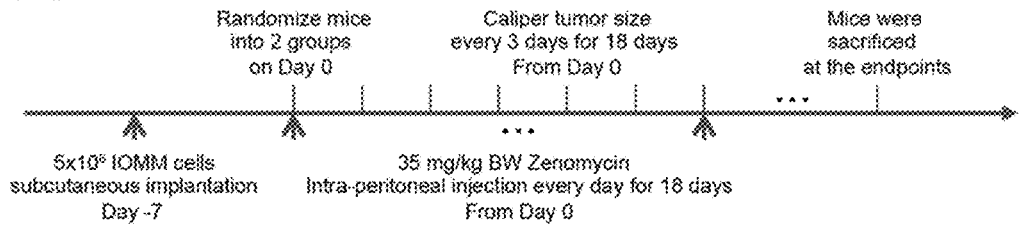
Figure 12G
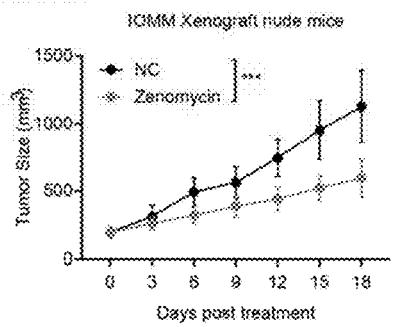
Figure 12H
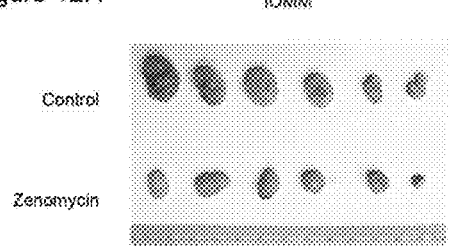

USE OF ISOVALERYLSPIRAMYCINS AS ANTI-CANCER AGENTS TO INHIBIT METASTASIS

This invention was made with Government support under project number Z01BC011773-01 by the National Institutes of Health, National Cancer Institute. The Government has certain rights in the invention.

TECHNICAL FIELD

The present invention relates generally to the field of oncology therapy, including but not limited to the treatment of malignant cancers, which are associated with a high risk of metastasis.

BACKGROUND

Conventional anticancer regimens typically exploit cell-killing functionalities, such as irradiation, chemotherapy and, more recently, T-cell activation or weaponization. This general approach can elicit off-target toxicities and other adverse side effects, such as a dysregulated immune response. An alternative approach therefore is needed whereby the mechanism of anticancer action relies less heavily on cell killing and its downstream consequences.

The need for new therapeutic approaches in this regard has prompted studies into employing antibiotic drugs as anti-cancer agents. For example, it has been determined that the anthracycline antibiotic doxorubicin is useable to treat a number of cancer types, Sun et al., *BMC systems biology* 11 (Suppl 5): 87, 100 (2017), possibly by the mechanism of intercalation into nuclear DNA and disruption of topisomerase-II-mediated DNA repair, resulting in cell death. Thom et al., *Pharmacogenetics & Genomics* 21: 440 (2011). Also, published international application WO 2007/144876 states that the macrolide antibiotics tylosin, erythromycin, and spiramycin can induce readthrough of a premature stop codon mutation in the APC gene, thereby enabling prevention or treatment of cancers, such as colorectal cancer and breast cancer, that harbor such APC mutations. See also published application US 2019/0350908, e.g., at paragraphs 0020 and 0035-0037, for disclosure that spiramycin and other aminoglycoside antibiotics can promote read-through of cancer cell mRNA bearing a premature stop codon, whereby the mRNA is translated into a neoantigen that in turn can induce an anticancer immune response.

Another line of investigation has focused on a group of recombinantly produced "hybrid antibiotics," so-called because they combine molecular features of two different macrolide antibiotics, spiramycin and carbomycin. See Abou-Zeid et al., *Zentralbl. Bakteriol. Naturwiss.* 135: 443 (1980), and Ashy et al., loc. cit. 541 (1980), respectively. Both antibiotics contain 16-membered lactone rings to which deoxysugars are attached: forosamine, mycaminose and mycarose for spiramycin; for carbomycin, mycaminose and a derivative of mycarose that contains an isovaleryl group at position 4. From a *Streptomyces* species that produces carbomycin, research groups in the United States and in China independently obtained a gene encoding an enzyme, 4"-O-isovaleryltransferase, which acylates the mycarose sugar. Epp et al., *Gene* 85: 293 (1989) (*S. thermotolerans* gene designated carE); Shang et al., *Chin. J. Biotechnol.* 15: 105 (1999) (*S. mycarofaciens* 1748 gene designated ist, with coding sequence "identical" to that of carE). As both groups showed, when the gene was introduced into a bacterial host that produces spiramycin, the recombinantly expressed transferase acted on the spiramycin as a substrate and converted it to a hybrid form, isovaleryl spiramycin. Id.

More specifically, researchers in China integrated the ist gene via homologous recombination into the chromosome of *S. spiramyceticus* F21, a spiramycin-producing strain. Shang et al. (1999), supra. The constructed strain WSJ-1 produced a "shengjimycin" complex of eleven 4"-acylspiramycins, the major components of the complex being 4"-isolvalerylspiramycin I, 4"-isolvalerylspiramycin II, and 4"-isolvalerylspiramycin III. Shang et al., *J. Antibiotics* 54: 66 (2001); Sun et al., *Actinomycetologica* 13: 120 (1999A). See also Sun et al., *Chinese J. Antibiotics* 25: 1 (1999B) (4"-isolvalerylspiramycin I isolated and characterized structurally, in comparison with 4"-isolvalerylspiramycin III).

As an antibiotic, the shengjimycin complex has been called "bitespiramycin" in the scientific literature, exemplified by Lu et al., *Microbial Cell Factories* 18: 38 (2019), and Shi et al., *J. Pharm. Biomed. Anal.* 36: 593 (2004), and "biotechspiramycin" in patent CN1174238. The name of the complex was normalized to "Carrimycin" by the Chinese Pharmacopoeia Commission in 2005.

China's National Medical Products Administration has approved Carrimycin as a new Class 1 drug for clinical antibiotic use by oral administration. Additionally, each of the above-mentioned major components of Carrimycin, 4"-isolvalerylspiramycin I, II and III, has been identified as an antibiotic in its own right, e.g., in U.S. Pat. No. 8,778,896.

More recently, there have been indications that Carrimycin and these same major components possess anticancer activity. Thus, published international applications WO 2018/184587, WO 2019/007368 and WO 2019/141254 together disclose data evidencing an inhibitory effect by Carrimycin and by each of 4"-isolvalerylspiramycin I, II and III on proliferation in vitro for a number of human cancer lines, among them breast cancer (MCF-7, MDA-MB-231), liver cancer (HepG2), non-small cell lung cancer (A549), large cell lung cancer (H460, H1299), renal clear cell adenocarcinoma (786-0), renal cell adenocarcinoma (769-P), glioma (U251), glioblastoma (A172), lymphoma (U937), cervical cancer (HeLa), prostate cancer (PC3), pancreatic cancer (PANC-1), esophageal cancer (TE-1), gastric adenocarcinoma (SGC-7901), colon cancer (HT-29), and promyelocytic leukemia (HL-60). Results in animal models are presented, too, that show a reduction caused by Carrimycin and by each of 4"-isolvalerylspiramycin I, II and III of various in vivo cancer parameters, such as tumor growth rate and relative tumor volume. Id. In addition, the '587 application references some clinical observations of favorable effects for human cancer patients who received Carrimycin.

According to WO 2019/141254, moreover, a pharmaceutical composition containing any one or more of 4"-isolvalerylspiramycin I, II and III, such as Carrimycin, possesses anticancer activity due to inhibiting the PI3K/AKT/mTOR pathway, which is frequently dysregulated in human cancers. Only a handful of PI3K/AKT/mTOR pathway inhibitors have been approved for clinical use, however, in part because such inhibitors "often have common on-target and off-target toxicities that are dose limiting, leading to the establishment of subtherapeutic maximum-tolerated doses." Janku et al., *Nat. Rev. Clin. Oncol.* 15: 273, 288 (2018). See also Morita et al., *Molecular Cell* 67: 922 (2017) (mTOR inhibition can protect cancer cells from death by countering increased mitochondrial fragmentation that implicated in some cancers).

SUMMARY OF THE INVENTION

The present inventors have discovered that pharmaceutical compositions that contain any one or more of 4"-isovalerylspiramycin I, II and III (collectively, "the isovalerylspiramycins" or "ISPs"), such compositions including but not limited to Carrimycin, act on cancer cells to trigger genomic instability, thereby inhibiting proliferation by promoting cell-cycle arrest. By virtue of this novel mechanism of action, using an ISP-containing pharmaceutical composition in accordance with the present invention affords reduced adverse side effects and finds application when such side effects are unsustainable, e.g., in treating end-stage cancer patients. Surprisingly, the novel mechanism of the invention is manifested as well in an inhibition of metastasis when a ISP-containing pharmaceutical composition is administered prophylactically, preferably but not necessarily beginning before and continuing after a primary cancer treatment.

More specifically, the inventors have discovered that the ISPs, individually or in any combination of two or three of them, target and suppress selenoprotein H (SELH), a nucleolus protein that contains a selenocysteine residue at its active site and that plays a pivotal role in protecting DNA from oxidative damage and mitigating genomic instability. See, e.g., Cheng and Cheng, *Curr. Devel. Nutrition* 3 (Suppl 1), nzz044.OR11-03-19 (2019); Short and Williams, *Adv. Cancer Res.* 136: 49 (2017); Cox et al., *Proc. Nat'l Acad. Sci. USA* 113: E5562 (2016). By inhibiting SELH in the nucleus, especially in the nucleolus, any of the ISPs induces accumulation of reactive oxygen species (ROS). Via the JNK2/TIF1A pathway in the nucleolus, moreover, the isovalerylspiramycins act to foster increased DNA damage and reduced RNA polymerase (Pol) I transcription, leading to inhibited cell proliferation and apoptosis in cancer cells. These effects at the molecular level result in an inhibition of tumor metastasis, regardless of the type of cancer that engenders the metastasis risk and that is the focus of the primary cancer treatment.

Accordingly, the present invention relates to a method for inhibiting metastasis comprising prophylactically administering to a subject who has a cancerous condition a medicament comprising (A) a compound selected from the group consisting of isovalerylspiramycin I, isovalerylspiramycin II and isovalerylspiramycin III or (B) a mixture comprising any two or more thereof, wherein said medicament is administered in a therapeutically effective amount to inhibit metastasis in the subject, who can be an end-stage cancer patient. The medicament can comprise any one or more of the aforementioned compounds. Pursuant to this method, the administering can occur before and/or after said treatment; for example, beginning before and continuing after the treatment. In particular, the administering of the medicament after the treatment can be chronic.

Pursuant to the invention, the cancerous condition can be characterized by nucleolar hypertrophy, can involve a tumor deficient for DNA damage repair, and/or can involve a cancer that displays accelerated rRNA synthesis. Illustrative of a cancerous condition addressed by the inventive method is one selected from the group consisting of melanoma, liver cancer, pancreatic cancer, blood cancer, brain cancer, breast cancer and colon cancer. In accordance with another aspect, the cancerous condition is selected from the group consisting of diffuse large B-cell lymphoma, acute myeloid leukemia, pancreatic adenocarcinoma, thyroid carcinoma, thymoma, uterine corpus endometrial carcinoma, uterine carcinosarcoma and uveal melanoma.

BRIEF DESCRIPTION OF THE DRAWINGS

FIGS. 1A-1C summarize in schematic form the organization of the Carrimycin biosynthetic gene cluster and the steps of ISP I biosynthesis. FIG. 1A depicts the chemical structure of Carrimycin and ISPs I, II and III. FIG. 1B depicts schematically the Carrimycin biosynthetic gene cluster, with the proposed functions of gene products indicated by various filling patterns, as indicated. FIG. 1C portrays a proposed pathway for ISP I biosynthesis, where "bsm44" denotes the 4"-O-isovaleryltransferase (ist) gene, which encodes an enzyme responsible for formation of an isovaleryl group at the 4" position.

FIGS. 2A-2F are a combined graphic and tabular presentation of ISP I's cytotoxicity for glioblastoma cells. FIG. 2A is a line graph of CCK8 assay data that delineate ISP I dose-response curves in relation to five glioblastoma cell lines, T98G, U118, A172, LN229 and U25, for a 48-hour period. FIG. 2B is a table that lists IC50 values calculated for each glioblastoma cell line. FIG. 2C depicts flow cytometry data that evidence the cell-cycle effect of ISP I treatment on LN229 and U251 cells. FIG. 2D presents in bar graph format a cell-cycle analysis showing G0/G1 arrest in ISP I-treated cells. FIG. 2E depicts flow cytometry data from an apoptosis (Annexin-V stain) analysis of LN229 and U251 cells with ISP I treatment. FIG. 2F presents in bar graph format results of apoptosis analysis (4 independent wells) of ISP I-treated LN229 and U251 cells. All data are shown as mean±s.e.m. P value: $*p<0.05$; $p<0.01$; $*p<0.001$.

FIGS. 3A-3D are a combined graphic and tabular presentation of the cytotoxicity in glioblastoma cells of ISP II and ISP III. FIG. 3A and FIG. 3C are line graphs of dose-response CCK8 data for ISP II and ISP III, respectively, for glioblastoma cells lines T98G, U118, A172, LN229 and U251. FIG. 3B and FIG. 3D are tables of IC50 values calculated for ISP II and ISP III, respectively, for each of the same cell lines.

FIGS. 4A-4F are a combined graphic, schematic and tabular presentation of the cytotoxicity of ISP I in renal cell carcinoma (RCC) cells. FIG. 4A is a line graph of dose-response CCK8 data for ISP I for RCC cell lines ACHN, UM-RC-2, RCC4 and 786-O for 48 hours. FIG. 4B is a table of IC50 values calculated for ISP I for each of the same cell lines. FIG. 4C depicts results from cell-cycle analysis of 786-O and RCC4 cells treated with ISP I. FIG. 4D presents bar graphs of cell-cycle progression data, showing clear G0/G1 arrest in ISP I-treated RCC cells. FIG. 4E portrays results from an Annexin-V apoptosis analysis of 786-O and RCC4 cells treated with ISP I. FIG. 4F summarizes in bar graph format results of the apoptosis analysis (four independent wells). All data are shown as mean±s.e.m. P value: $*p<0.05$; $p<0.01$; $*p<0.001$.

FIGS. 5A-5M are combined schematic and graphic presentation of ISP I's targeting to SELH in glioblastoma cell lines. FIG. 5A is a schematic summary of a Drug Affinity Responsive Target Stability (DARTS) assay. FIG. 5B presents western blotting results for SELH expression in LN229 cells, showing that ISP I-protected SELH was observed along with the rise of temperature, while SELH in a DMSO-treated group decreased significantly. FIG. 5C is a line graph depicting surface plasmon resonance (SPR) analysis of the interaction between ISP I Zenomycin with antioxidant components, including SELH, synthesized in bacteria. FIG. 5D presents western blots showing the decline, in a dose-dependent manner, of SELH levels in ISP 1-treated LN229 cells at 24 hours post-treatment. FIG. 5E presents western blots that show decreased SELH levels in ISP I-treated glioblastoma cell lines (T98G, U118, LN229, and U251) after treatment with 10 µg/mL of ISP I for 24 hours. FIG. 5F presents results from a cycloheximide pulse chase assay and immunoblotting, which evidence a decrease of SELH protein half-life in ISP I-treated LN229 cells. FIG. 5G is a line graph that quantifies immunoblot band results from FIG. 5F. FIG. 5H depicts results, obtained by knocking out SELH in LN229 cells (KO #2), showing a resistance to ISP I and, from western blots, no detectable SELH expression; calculated IC50 values also are tabulated. FIG. 5I presents data from a knock-down of SELH in LN229 cells, resulting in a decrease of cell proliferation. Western blots show no detectable expression of SELH in the LN229 cells two days after SELH siRNA transfection. As a control, a CCK8 assay was performed to measure cell proliferation for wild-type LN229 cells. FIG. 5J depict cell-cycle analysis data for SELH-deficient LN229 and U251 cells. FIG. 5K depicts flow cytometry data that evidence G0/G1 arrest in the SELH-deficient LN229 and U251 cells. FIG. 5L shows flow cytometry data from an apoptosis (Annexin-V stain) analysis of SELH-deficient LN229 and U251 cells with ISP I treatment. FIG. 5M presents in bar graph format results of apoptosis analysis (four independent wells) of the SELH-deficient LN229 and U251 cells. Expression of GAPDH served as an internal control in FIGS. 5D-F, H and I. All data are shown as mean±s.e.m. P value: *$p<0.05$; $p<0.01$; *$p<0.001$.

FIGS. 6A-6G are a combined graphic, schematic and tabular presentation of ISP I's targeting to SELH in RCC cells. FIG. 6A depicts wester blotting results for SELH expression in 786-O cells. ISP I-protected SELH was observed along with a rise in temperature, while SELH decreased significantly with DMSO treatment. FIG. 6B portrays western blots that show decreased SELH levels in 786-O and RCC4 cells after treatment with ISP I (10 µg/ml) for 24 hours. FIG. 6C provides an overview of results from SELH knock out in 786-O and RCC4 cells, resulting in resistance to ISP I. Western blots show low expression of SELH in the RCC cells. The tabulated values compare ISP I IC50 for wild-type and knock-out cells from each RCC line. FIG. 6D depicts data from a cell-cycle analysis of SELH-deficient 786-O and RCC4 cells. FIG. 6E provides in bar graph format an overview of cell-cycle progression data, showing clear G0/G1 arrest in SELH-deficient cells. FIG. 6F portrays results from an Annexin-V apoptosis analysis of SELH-deficient 786-O and RCC4 cells treated with ISP I. FIG. 6G summarizes in bar graph format results of the apoptosis analysis (four independent wells). Expression of GAPDH serves as an internal control in FIGS. 6B and 6C. All data are shown as mean±s.e.m. P value: *$p<0.05$; $p<0.01$; *$p<0.001$.

FIGS. 7A-7I are a combined graphic and schematic presentation of ISP I's causing ROS accumulation. FIG. 7A is a bar graph of data from a glutathione peroxidase activity assay, showing a decrease, in a dose-dependent manner, of SELH enzyme activity in LN229 cells treated with ISP I. FIG. 7B is a bar graph that quantifies data on ROS levels from a ROS-Glo H2O2 assay for the LN229 cells of FIG. 7A, treated with ISP I at 10 µg/mL for 24 hours. All groups were normalized to saline-treated groups. FIG. 7C presents data from flow cytometry analysis of ROS level using MitoSOX staining, which data show an increase of mitochondrial ROS accumulation in ISP I-treated glioblastoma cell lines (LN229 and U251). Cells were pre-treated with 5 µg/mL or 10 µg/mL ISP I for 24 hours. FIG. 7D is a bar graph of data on ROS levels from three independent wells. FIG. 7E is a bar graph of real time RT-PCR data showing an increase in NRF2 expression in LN229 and U251 cells treated with 10 µg/mL ISP I for 24 hours. 18s expression served as an internal control. FIG. 7F depicts in bar-graph format real time RT-PCR results that show an increase of the expression of NRF2 downstream genes HMOX1 and NQO1, with 18s as an internal control. FIG. 7G presents western blot data evidencing that overexpression of SELH in LN229 and U251 cells caused down-regulation of NRF2, while knocking down of SELH increased NRF2 expression. GAPDH expression was used as an internal control. FIG. 7H is a bar graph of real time RT-PCR results, showing a slight increase of NRF2 mRNA upon knock down of SELH in U251 cells. FIG. 7I is a bar graph of data showing that the downstream gene HMOX1 was unregulated in SELH-knockdown LN229 and U251 cells. All data are shown as mean±s.e.m. P value: *$p<0.05$; $p<0.01$; *$p<0.001$.

FIGS. 8A and 8B depict, respectively, immunofluorescence staining assay data and western blot data showing an increase of γH2AX expression in LN229 and U251 cells treated with ISP 1 for 6 hours in a dose dependent manner. Expression of GAPDH served as an internal control. FIG. 8C presents immunofluorescence staining assay data showing an increase of R-Loops formation and a reduction in EdU incorporation by U2OS cells treated with ISP 1 for 6 hours in a dose dependent manner. FIGS. 8D and 8E are quantitative graphic representations that compare the aforementioned effects on DNA replication and R-loop formation, respectively. All data are shown as mean±s.e.m. P value: *$p<0.05$; $p<0.01$; *$p<0.001$.

FIGS. 9A-9G are a combined graphic and schematic presentation of ISP I's resulting in ROS accumulation and DNA damage in RCC cells. FIG. 9A is a bar graph of ROS-Glo H$_2$O$_2$ assay results showing ROS levels for RCC cells treated with ISP I (10 µg/ml) for 24 hours. All groups were normalized to saline-treated groups. FIG. 9B depicts data from flow cytometry analysis of ROS level using MitoSOX staining, showing an increase in mitochondrial ROS accumulation in ISP-I-treated RCC cells. Cells were pre-treated with 5 µg/ml or 10 µg/ml ISP I for 24 hours. FIG. 9C presents in bar graph format the ROS level data from three independent wells. FIG. 9D is a bar graph of real time RT-PCR data showing an increase in NRF2 expression in RCC cell lines 786-O and RCC4 upon treatment with ISP I (10 µg/ml) for 24 hours. 18s expression serves as an internal control. FIG. 9E depicts in bar graph format real time RT-PCR results, showing an increase in expression of the NRF2 downstream genes HMOX1 and NQO1, with 18s as an internal control. FIG. 9F presents in photomicrograph format immunofluorescence staining assay data, and FIG. 9G depicts western blots, that show an increase of γH2AX expression in 786-O and RCC4 cells treated with ISP I for 6 hours in a dose-dependent manner. All data are shown as mean±s.e.m. P value: *$p<0.05$; ***$p<0.001$.

FIG. 10A depicts immunofluorescence staining assay data showing a loss in ISP I-treated LN229 cells (8 h, 10 µg/mL) of SELH and nucleolar labeling of Nucleolin, Fibrillarin, POL1 and NPM. FIG. 10B presents results from western blotting that show that ISP I decreased nucleolar protein, NPM and P53 expression in a dose dependent manner. GAPDH expression was used as an internal control. FIG. 10C is a bar graph of data from Real-time RT-PCR analysis, revealing decreased pre-rRNA transcription in a dose-dependent manner. GAPDH serves as an internal control. FIG. 10D presents western blotting results showing that ISP I increased JNK2 phosphorylation, while slightly reducing POL1 and TIF1A expression in a dose-dependent manner. GAPDH expression was used as an internal control. FIG. 10E presents results obtained with immunoprecipitation effected by anti-TIF1A antibody, showing that POL1 interacted with TIF1A in LN229 cells. FIG. 10F is a bar graph of data from quantitative CHIP evaluations showing that ISP I treatment or deficiency of SELH reduces the occupancy of POL1 on rNDA through the promoter and the coding region. All data are shown as mean±s.e.m. P value: *p<0.05; p<0.01; *p<0.001.

FIG. 11A is a schematic diagram of the progression of in vivo experimentation in this regard. NSG mice received intracranial injection of $1 \times 10^5$ LN229-luc cells. Seven days after implantation, the resultant tumors were imaged and mice were randomized into two groups: untreated (N=8) and ISP I-treated (N=8). The mice were injected intraperitoneally with ISP I (66 mg/kg body weight) every day. FIG. 11B is a line graph of results from bioluminescence imaging that was used to follow tumor progression. The luminescence signal showed reduced LN229-luc tumor burden compared with the untreated group; p value was calculated by two-way ANOVA (****p<0.001). FIG. 11C presents tumor-derived bioluminescence images for three mice, showing a complete response induced by ISP I on day 24. FIG. 11D is a schematic diagram showing progression of the in vivo experiment. C57/B16 mice received tail vein injection of $2 \times 10^5$ murine B16 cells on day 0. Mice were randomized into three groups: untreated (N=9), ISP I-treated (N=9) group, and Carrimycin-treated (N=9). Every day the mice were injected intraperitoneally with ISP I (35 mg/kg body weight) or were subjected to oral gavage with Carrimycin (56 mg/kg). After 12 days, the lungs were photographed and the melanoma spots on the lung were counted, as shown in FIGS. 11E and 11F, respectively. With reference to FIGS. 11G, 11H and 11I, the knock out of SELH in B16 cells resulted in a significant decrease of lung metastasis. Thus, FIG. 11G presents western blots showing no detectable expression of SELH in the B16 cells. FIG. 11H presents photographs taken of the lungs at 12 days after tail vein injection of B16 or SELH-deficient B16 cells (N=5 per group), and FIG. 11I depicts the results when melanoma spots on the lungs were counted. All data are shown as mean±s.e.m. P value: *p<0.05; p<0.01; *p<0.001.

FIGS. 12A-12I1 are a combined graphic, schematic, tabular and photomicrographic presentation of ISP I's suppressing tumor growth in RCC and meningioma xenograph mouse models. FIG. 12A is a schematic diagram of the in vivo experiment. NSG mice were injected subcutaneously in the flank with 786-O cells ($1 \times 10^7$). One week later the tumor-bearing mice were randomly assigned to two groups and treated daily with normal saline or ISP I (35 mg/kg), administered intraperitoneally. FIG. 12B is a line graph of tumor volume data, calculated based on caliper measurements. The tumor growth curve shows reduced 786-O tumor burden compared with the untreated group; p value was calculated by two-way ANOVA (*p<0.001). FIG. 12C shows, for 786-O xenograft, photographic images of tissue samples from control and ISP I groups, with corresponding tumor-weight data in bar graph format. Tumors were excised and weighed at the end of the experiment (18 days after treatment). FIG. 12D is a line graph of CCK8 results that delineate an ISP I dose-response curve for each of three meningioma cell lines, IOMM, JEN and CH-157, for 48 hours. FIG. 12E is a table listing IC50 values calculated for each of the aforementioned cell lines. FIG. 12F is a schematic diagram of the experiment in vivo. Nude mice were injected subcutaneously in the flank with IOMM cells ($5 \times 10^6$). One week later the tumor-bearing mice were assigned randomly to two groups and were treated daily with normal saline or ISP I (35 mg/kg), administered intraperitoneally. FIG. 12G is a line graph of data showing the effect of ISP I on tumor size. Tumors were measured with a caliper and volume was calculated. The tumor growth curve reflected a reduced IOMM tumor burden compared with the untreated group; p value was calculated by two-way ANOVA (*p<0.001). FIG. 12H provides a photographic comparison, for control group versus ISP I group, of IOMM xenograft tumor size. Tumors were excised and weighed at the end of the experiment (18 days after treatment). All data are shown as mean±s.e.m.

DETAILED DESCRIPTION

Therapeutic Paradigm and Definitions

Figure 8A:
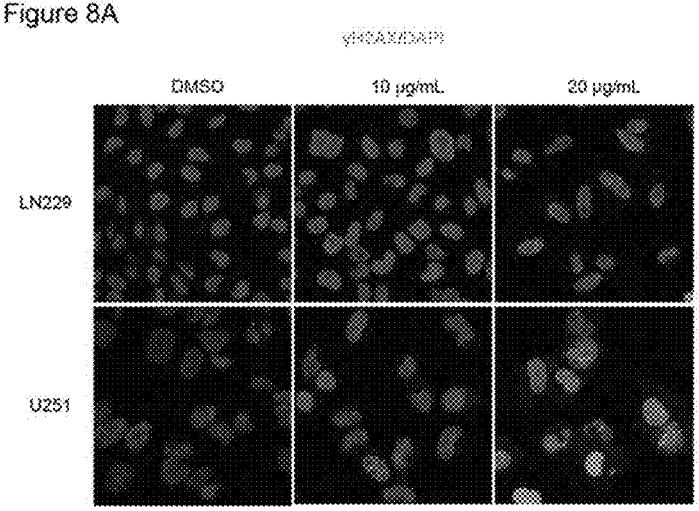
FIGS. 8A-8E are a combined photomicrographic and schematic presentation of ISP 1's resulting in DNA damage.
Figure 8B:
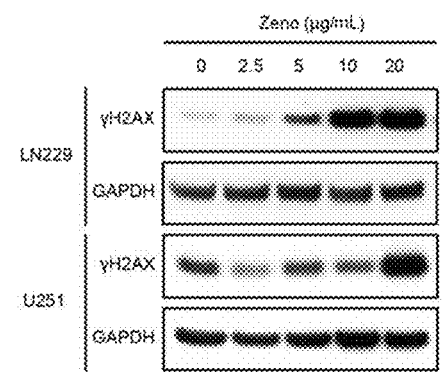

Cancer metastasis is the process by which cancer cells spread from one organ, "the primary," to another non-adjacent organ or organs. More specifically, in the metastatic process a subpopulation of cancer cells within the primary adapt to selective pressures that allow those cells to spread, invade and flourish in hostile, non-native environments. METASTATIC CANCER: CLINICAL AND BIOLOGICAL PERSPECTIVES, R. Jandial (ed.), Landes Bioscience (2013). Medical complications arising from metastatic growth, such as hemoptysis, jaundice and seizures, "are responsible for the bulk of morbidity and mortality suffered by cancer patients and represent the majority of clinical problems that oncologists face," including how to eradicate or at least shrink metastases and to palliate their complications. Id.

In fact, conventional chemotherapy and molecular therapy options for metastatic cancers in general offer only modest improvement in clinical outcome. Frankowski et al., *Sci. Transl. Med.* 10: eaap8307 (2018). Accordingly, there are lines of research, illustrated by He et al., *Cell Report* 30: P714 (2020), Carlson et al., *Nat. Cell Biol.* 21: 238 (2019), and Frankowski et al. (2018), supra, that seek an approach to inhibiting metastasis itself. Results on point are still preliminary, however, and may not be readily generalized beyond certain cancers. Thus, an unmet need remains for a therapeutic paradigm to inhibit metastasis across the range of cancerous conditions associated with a substantial risk of metastasis.

In the present description, the term "metastasis" is amply defined above with reference to its widely accepted clinical oncology meaning. When it speaks of "inhibiting" metastasis, this description refers to disrupting the metastatic process so as to diminish the risk to a subject, including a human cancer patient, that cancer cells associated with a cancerous condition affecting the subject will spread, invade and proliferate in another, non-adjacent site in the subject's body.

Instead of administering a pharmaceutical active that acts as an external agent for direct DNA damage, in keeping conventional practice, the claimed method employs an ISP-containing medicament that in effect, as illustrated below, tips a SELH-mediated nucleolar system for countering DNA damage so that endemic damage accrues, leading to an inhibition of metastasis via cell-cycle arrest and apoptosis due to DNA-damage signaling. This approach avoids the undesirable toxicity of using conventional cell-killing actives. It also focuses on cancer cells as such, since they evince a vulnerability in SELH levels that generally are higher than those in normal (non-cancer) cells, as shown by reference to SELH mRNA expression levels in the Gene Expression Profiling Interactive Analysis (GEPIA) database (accessible at http://gepia.cancer-pku.cn/). In particular, SELH is highly expressed in malignant tumors, such as glioblastoma, and in metastatic tumors, i.e., breast cancer, melanoma, and others.

Accordingly, the phrase "cancerous condition" in this description encompasses any and all malignant cancers, especially but not limited to primary tumors that are poorly differentiated or undifferentiated and that are associated with poor patient outcomes, such as melanoma, liver cancer, pancreatic cancer, blood cancer, brain cancer, breast cancer and colon cancer. Within the ambit of "cancerous condition" are malignancies characterized by nucleolar hypertrophy (enlarged nucleoli), since nucleolar size has been shown to be a valid prognostic parameter in neoplastic diseases. Penzo et al., *Cells* 8: 55 (2019), citing Derenzini et al., *Histopathology* 54: 753 (2009). "Cancerous conditions" also encompasses the subgenus of cancers, including but not limited to diffuse large B-cell lymphoma, acute myeloid leukemia, pancreatic adenocarcinoma, thyroid carcinoma, thymoma, uterine corpus endometrial carcinoma, uterine carcinosarcoma and uveal melanoma, that are characterized, e.g., through gene expression profiling, by a level of SELH expression exceeding the median level for cancers generally (see GEPIA database, supra). Another subgenus within the category of "cancerous conditions" includes homologous recombination-deficient and non-homologous end joining-deficient cancers and other tumors deficient for DNA damage repair, such as TP53, ERCC1, PMS2 and XPF mutation-related cancers (see Bernstein et al., "DNA Damage, DNA Repair and Cancer" in NEW RESEARCH DIRECTIONS IN DNA REPAIR, C. Chen ed. (IntechOpen 2013)), which as a group are vulnerable to impairment, pursuant to the present invention, of that above-mentioned nucleolar system for countering DNA damage. Yet another subgenus within "cancerous conditions" includes cancers, such as glioblastoma, that display accelerated rRNA synthesis, a marker for aggressive cancer cells (see Kofuji et al., *Nature cell biology* 21: 1003 (2019)).

The present invention thus relates to inhibiting metastasis, in a subject with a cancerous condition, by administering to the subject, before or after the subject receives treatment for the condition ("the primary cancer treatment"), a medicament comprising at least one ISP. The primary cancer treatment can be any manner of medical intervention directed against the cancerous condition, such as surgical resection, irradiation, chemotherapy, immunotherapy, or some combination thereof.

In this regard, the administration of medicament can be combined with another therapeutic regimen that may be undertaken before and/or after the primary cancer treatment, e.g., preoperative chemotherapy and/or radiotherapy, see Hong et al., *Cancer biology & therapy* 16: 821 (2015), and neoadjuvant (presurgical) immunotherapy, see Topalian et al., *Science* 367: eaax0182 (2020). The administration of medicament also can be combined with pre- and/or post-treatment diagnostic testing, such as immune profiling and the like that surveils for changes in the immune system that are indicative of tumor status and/or the probability of or progress toward a pathologic complete response.

In this context, the term "administering" includes oral administration and intravenous administration of the medicament. The term "medicament" denotes a pharmaceutical composition comprised of one or more ISPs and a carrier or excipient therefor, along with any other constituent that is suitable for such a composition, e.g., an adjuvant, a solubilizer, a stabilizer, a buffer, a tonicity modifier, a bulking agent, a viscosity enhancer or reducer, a surfactant, and a chelating agent. The dosage form of the medicament can be tablet (including sugar-coated tablet, film-coated tablet, sublingual tablet, orally disintegrating tablet, buccal tablet and the like), pill, powder, granule, capsule (including soft capsule and microcapsule), troche, syrup, liquid, emulsion, suspension, release control preparation (e.g., immediate-release preparation, sustained-release preparation, sustained-release microcapsule), film (e.g., orally disintegrating film, oral mucosa-adhesive film), injectable (i.e., for intravenous injection), and drip infusion. Formulations of Carrimycin and each of the ISPs are exemplified in various dosage forms—tablet, capsule, dry syrup, granule, freeze-dried powder—in WO 2018/184587 and WO 2019/007368, the contents of which are incorporated herein by reference.

Pursuant to the invention, the administering of the ISP-containing medicament is done prophylactically, in the sense of secondary prophylaxis: a subject already at risk of metastasis undergoes administration with the medicament in order to inhibit a worsening of subject's condition through an incidence of metastasis. In this regard, the medicament can be administered before the primary cancer treatment, e.g., one, two, three, four, five, six, seven or more days before the medical intervention mentioned above, and/or after the primary cancer treatment. Post-treatment administration of medicament can continue for a period of weeks or months, in order to reduce the risk of recurrent cancer after administration ceases. With an emphasis on the latter consideration, post-treatment administration can be chronic, as opposed to acute or subacute. Thus, the medicament is administered over a period of three months or more, e.g., for six months or more, including but not necessarily for the remainder of the subject's life. It is a significant advantage of the present invention that such protracted administration is feasible for the ISP-containing medicament because of its surprisingly low toxicity and the consequent reduction of adverse side effects.

Furthermore, the medicament is administered in "a therapeutically effective amount," i.e., in a single dose or in multiple, divided subdoses at a suitable interval, e.g., two, three or more subdoses over a day or another appropriate schedule, to a prescribed total amount of active, such that metastasis is inhibited in the subject. Like the dose schedule, the effective amount of medicament will depend on a variety of factors, including the age and condition of the subject, the nature and extent of the cancerous condition, any contraindications, and the pharmacokinetic and pharmacodynamic characteristics of the medicament. For example, based on an accepted guide to animal-to-human dose conversion, see Nair R. Jacob, *J. Basic. Clin. Pharm.* 7: 27 (2016), the preclinical data detailed below implicate a therapeutically effective intravenous dose for Carrimycin of about 4.2 milligrams per kilogram of human body weight (BW), and about 2.8 mg/kg BW for ISP I. Although dosage and dosing schedule will be informed for any given patient by clinical testing of the particular ISP-containing medicament used, an amount of active in excess of about 8 to 10 mg/kg BW may be deemed problematic in view of the preclinical observation that a doubling of the aforementioned i.p. dose of ISP I caused severe diarrhea in mice upon one week of continuing administration. In addition, other preclinical data discussed below suggest a lesser potency for ISP II and ISP III, respectively, compared to ISP I, which is a factor that would figure in the formulation and administration of medicaments containing ISP II and/or ISP III pursuant to the present invention.

As mentioned above, the ISPs employed in accordance with the present invention can be obtained from *Streptomyces* species bacteria that in wild type produce spiramycin endogenously, such as *S. spiramyceticus* and *S. ambofaciens*, and that are modified to express a 4"-O-transferase gene from a *Streptomyces* species that produces carbomycin, such as *S. mycarofaciens, S. thermotolerans* and *S. halstedii*. For example, see Shang et al. and Epp et al., supra. In relation to such bacterial constructs, there are known approaches for enhancing the production of ISPs generally, see Li et al., Braz. *J. Microbiol.* 40: 734 (2009) (improved ISP production upon increase in exogenous leucine), Wang et al., *Bioprocess Biosyst. Eng.* 33: 257 (2010) (glucose limitation enhances ISP production), and Zhang et al., *Chinese J. Biotech.* 30: 1390 (2014) (in ISP-producing construct, ist gene expression enhanced by introducing positive regulatory gene system of midecamycin 4"-propionyltransferase (mpt) gene); known approaches, too, for favoring the production of one ISP over others, see Ma et al., *Curr. Microbiol.* 62: 16 (2011), and published Chinese application CN101054553 (disrupting or blocking 3-O-acyltransferase in ISP-producing construct results in production of ISP I over ISPs II and III), and Lu et al., *Microb. Cell Fact.* 18: 38 (2019) (disruption of leucine-responsive regulatory protein in *S. spiramyceticus* 1941 was advantageous for production of bitespiramycin, especially its ISP 3 component). In addition, gene editing rather than homologous recombination can be employed to produce ISP-producing bacteria. For instance, see Zhang et al., *Chinese J. Biotech.* 35: 472 (2019) (with CRISPR-Cas9 gene editing, an ISP I-producing strain is constructed, without resistant gene markers, by replacing bsm4 gene with ist gene under control of constitutive promoter ermEp*).

Production of a multicomponent, ISP-containing fermentation broth as described above typically is followed by a partial purification involving preparative high-performance liquid chromatography (HPLC) or comparable methodology, such the membrane extraction technique disclosed by Hossain et al., *J. Chem. Technol. &Biotech.* 86: 1247 (2011), to obtain a pharmaceutically acceptable composition, such a Carrimycin, which contains ISPs and other components that do not impair the metastasis-inhibiting activity of the composition. Such a composition is said to "consist essentially of" its ISP components. Additional purification, e.g., involving silica gel column chromatography as disclosed by published Chinese patent application CN101785778, then can be carried out to obtain (A) a more refined ISP mixture or (B) any of ISP I, ISP II and ISP III in greater than about 95% purity ("pharmaceutical grade purity"), whereupon any one, two or three of these can be formulated into a desired dosage form, as described above.

Carrimycin Structure and Synthesis

As noted above, Carrimycin is a hybrid macrolide antibiotic that China's National Medical Products Administration has approved for human use. The approved drug is produced by recombinant *S. spiramyceticus* bacteria that express a 4"-O-isovaleryltransferase gene from *S. thermotolerans*, designated the ist gene. Due to the low specificity of the 4"-O-isovaleryltransferase and 3-O-acytransferase, which is involved in spiramycin biosynthesis, the composition of Carrimycin is heterogenous and primarily comprise ISPs and a trace amount of 4"-acyl spiramycin components (FIG. 1A).

Compared with spiramycin, Carrimycin has a longer half-life, higher potency, and better tissue penetration and pharmacokinetic characteristics. Shi et al., *Xenobiotica* 35: 343 (2005); Shi et al., *Acta pharmacologica Sinica* 25: 1396 (2004). Genomic sequencing of the Carrimycin-producing bacterial strain revealed its biosynthetic gene cluster, which consists of a length of approximately 90 Kb (Genbank accession number MH460451) (FIG. 1B). The gene cluster was divided into two groups: (i) a spiramycin biosynthetic gene cluster and (ii) heterologous ist genes for 4"-isovalerylation of spiramycin. Further biosynthetic analysis revealed that the structural backbone of Carrimycin is a polyketide, designated "platenolide I" (FIG. 1C), which is dependent on polyketides synthase (PKS) and malonyl-CoA for its biochemical composition. After several post-PKS tailoring steps, including glycosylation, oxidation, acylation and isovalerylation, a heterogenous mixture is produced that comprises the isovalerylspiramycins I, II and III, distinguished only by different acyl substitutions of the hydroxyl group on carbon 3 (FIG. 1C).

Cytotoxicity of Carrimycin and ISPs In Vitro

To assess the cytotoxicity of ISPs I, II and III, five glioblastoma cell lines, T98G, U118, A172, LN229 and U251, were treated with serial doses of each ISP, respectively, for 48 hours. Cell viability of these cell lines were evaluated by CCK8 assay, and the 50% inhibitory concentration (IC50) was calculated (FIG. 2A, B and FIG. 3). All glioblastoma cell lines were more sensitive to ISP I when compared to ISPs II and III. Out of the glioblastoma cell lines tested, LN229 appeared to be the most sensitive to Carrymycin's cytotoxic effect, while U251 appeared the least sensitive. Cell distribution in each phase of the cell cycle was assessed in LN229 and U251 cells by flow cytometry, followed by EdU and DAPI staining. The cell cycle analysis showed that ISP I resulted in a dose-dependent increase in the G0/G1 phase and a decrease in the S phase compared with the control cells (FIG. 2C, D). This finding indicates that treatment with ISP I induced a cell cycle arrest at the G0/G1 phase in treated cells. Further flow cytometric assessment with Annexin V stain, a marker for cell apoptosis, revealed that ISP I induced a dose-dependent apoptosis in treated cells (FIG. 2E, F).

To confirm the cytotoxic effect observed in the glioblastoma cell lines, the inventors assessed ISP I's effect on renal cell carcinoma (RCC) cell lines (ACHN, UM-RC-2, RCC4 and 786-0). Cell viability was assessed similarly via CKK8 analysis. Out of the RCC cell lines tested, ACHN appeared to be the most sensitive to ISP I's cytotoxic effect while 786-O demonstrated to be the least sensitive (FIG. 4A, B). Consistent with glioblastoma cell line findings, flow cytometric analysis revealed that ISP I induced cell-cycle arrest in the G0/G1 phase in treated cells and likewise induced a dose-dependent apoptosis in treated cells. (FIG. 4C, D). Taken together, these results indicate that ISP I inhibits cell proliferation by arresting cancer cells in the G0/G1 phase and inducing tumor cell apoptosis.

ISP I Targets to Selenoprotein H

To identify ISP I's molecular target, the inventors performed drug affinity responsive target stability (DARTS) assay in LN229 cells. The basic strategy of DARTS is shown in FIG. 5A.

The inventors discovered that the binding of ISP I to its target proteins temporarily locks them into a stable conformational structure, which prevents their recognition by proteases. After evading protease degradation, the identity of ISP I's target proteins was determined using mass spectroscopy. DARTS analysis results revealed that SELH was the most abundant primary protein present in ISP I-treated LN229 cells.

Next, the inventors used a thermo-stability assay to confirm SELH was targeted by ISP I in LN229 and 786-O cell lines. The principle of the assay is based on altered protein thermal stabilization/destabilization due to ligand binding in living cells. Indeed, western blot results demonstrated that the protective effect of ISP I on SELH was present over a range of increasing temperatures, an effect that was significantly decreased in the SELH from DMSO-treated groups. (FIG. 5B and FIG. 6A). To verify further the specificity of ISP I's targeting of SELH, the inventors designed a surface plasmon resonance assay to assess the interaction of ISP I with SELH synthesized in bacteria. These results show that ISP I tightly binds to SELH but does not bind with the other proteins (FIG. 5C). Accordingly, the results indicate that the molecular target of ISP I is SELH.

To explore ISP I's effect on SELH, the inventors assessed the quantity of SELH protein in LN229 cells treated with different concentrations of ISP I. Treatment with ISP I reduced SELH protein expression in LN229 cells in a dose-dependent manner (FIG. 5D). ISP I's inhibitory effect on SELH expression also was confirmed in four glioblastoma cell lines, T98G, U118, LN229 and U251, and in two RCC cell lines, 786-O and RCC4 (FIG. 5E and FIG. 6B). A cycloheximide (CHX) chase assay was completed to assess ISP I's effect on SELH protein degradation. The CHX chase assay results confirm that treatment with ISP I reduced the SELH protein half-life, evidencing that ISP I promotes SELH protein degradation (FIG. 5F, G).

To confirm further that ISP I inhibits cell growth via a SELH-dependent mechanism, the inventors generated SELH-deficient LN229 cells and RCC cells (786-O and RCC4) with CRISPR/CAS9 and then treated them with ISP I. CCK8 assay results demonstrated that SELH-deficient cells were resistant to ISP I treatment when compared to wild-type LN229 cells (FIG. 5H and FIG. 6C). Next, the inventors knocked down SELH expression using siRNA in two glioblastoma cell lines (LN229 and U251) and two RCC cell lines (786-O and RCC4) to assess ISP I's effect on cell growth, proliferation and apoptosis. siRNA mediated knockdown of SELH resulted in a significantly decreased growth rate of LN229 cells (FIG. 5I) and significantly inhibited cell proliferation and apoptosis in the glioblastoma (LN229 and U251) and RCC cell lines (786-O and RCC4) (FIGS. 5J-M and FIGS. 6D-G). Together these data demonstrate that ISP I inhibited glioblastoma and RCC cell growth through the suppression of SELH expression.

ISP I Results in ROS Accumulation

ISP I-treated LN229 cells demonstrated significantly reduced glutathione peroxidase activity (FIG. 7A). Since glutathione peroxidase catalyzes the reduction of reactive oxidative species (ROS), the inventors assessed whether treatment with ISP I increased the generation of ROS in glioblastoma cell lines (LN229 and U251) and RCC cell lines (786-O and RCC4). ROS-Glo H2O2 assay analysis confirmed that ISP I treated cells exhibited increased intracellular ROS levels (FIG. 7B and FIG. 9A). MitoSOX staining followed by flow cytometric analysis revealed that ISP I-treated glioblastoma and RCC cells generated higher intracellular ROS in a dose-dependent manner (FIG. 7C, D and FIG. 9B, C).

NRF2 (NFE2L2) is a transcription factor that regulates redox homeostasis by binding to the regulatory regions of antioxidant response elements (ARE). Since ISP I-treated cells demonstrated increased intracellular ROS, the inventors assessed if ISP I altered the NRF2 antioxidant pathway. Glioblastoma (LN229 and U251) cells and RCC (786-O and RCC4) cells were treated with ISP I and evaluated for NRF2 expression levels. Real-time (RT) PCR demonstrated that NRF2 expression was significantly upregulated in ISP I treated groups (FIG. 7E and FIG. 9D). Additionally, RT-PCR confirmed a significant increase in the downstream targets of NRF2 signaling, namely, HMOX1 and NQO1 (FIG. 7F and FIG. 9E). Considering this finding, the inventors evaluated SELH's regulatory role on NRF2 by measuring NRF2 expression in cells that either overexpressed or had silenced SELH expression. Western blots showed that overexpression of SELH decreased NRF2 protein level, while cells with silenced SELH expression demonstrated increased NRF2 protein levels (FIG. 7G). RT-PCR demonstrated a slight increase in NRF2 mRNA in SELH-silenced U251 cells (FIG. 7H). In contrast, HMOX1 mRNA increased significantly in SELH-silenced cells, consistent with an increase of NRF2 protein in this group (FIG. 7I). These data indicate that ISP I induces ROS accumulation and activates antioxidative signaling, including NRF2 pathway.

ISP I Results in Genomic Instability

It is well-established that increased levels of ROS in cells leads to oxidative DNA damage, inducing genomic instability and inhibiting cell cycle progression. Cooke et al., FASEB J. 17: 1195 (2003). Since ISP I downregulates SELH, a key regulator of ROS response elements, the inventors first assessed whether treatment with ISP I augmented DNA damage in vitro. Immunofluorescence staining and western blot analysis results revealed that ISP I-treated LN229 and U251 cells demonstrated higher quantities of γH2A.X, a marker of DNA damage (FIG. 8A, B and FIG. 9F, G).

Figure 8C:
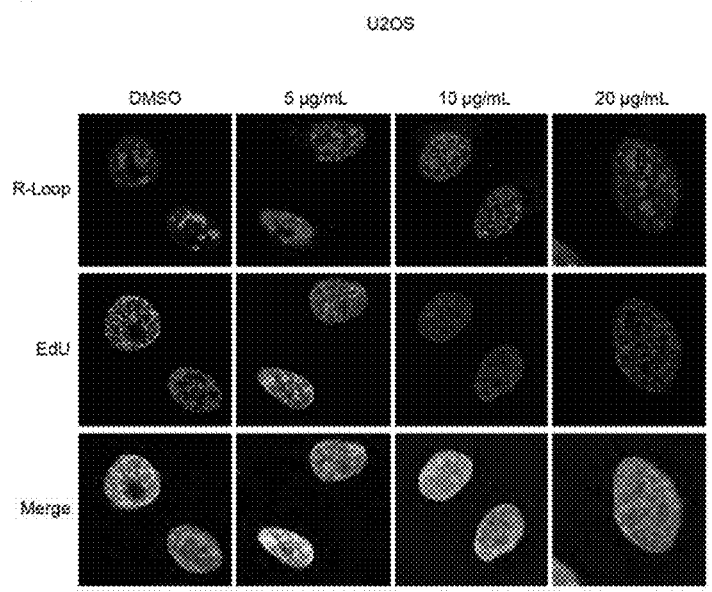
Figure 8D:
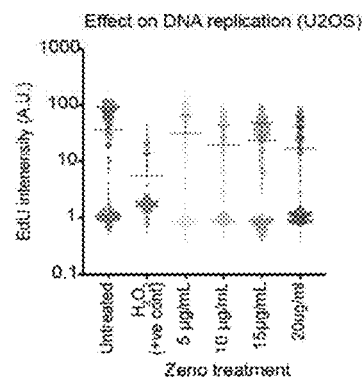
Figure 8E:
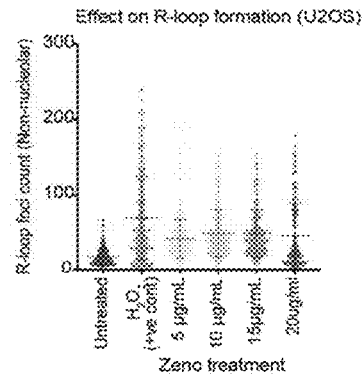

In order to assess ISP I's effect within the nuclear compartment, the inventors evaluated DNA-RNA R-loop formation within ISP I-treated Human Bone Osteosarcoma Epithelial Cells (U2OS cell line). R-loops are DNA-RNA hybrid structures composed of a displaced single-stranded DNA hybridized with the nascent RNA transcript. Santo-Pereira et al., Nat. Rev. Genet. 16: 583 (2015). The formation of R-loops is strongly induced by ROS in the transcript region and may block DNA replication and result in DNA damage. Teng et al., Nature communications 9: 4115 (2018). Using a U2OS cell line overexpressing the RaseH-V5 (R-Loop marker), the inventors discovered that ISP I increased R-loop accumulation and also reduced EdU (DNA replication marker) incorporation into DNA in a dose-dependent manner (FIG. 8C-E).

Figure 10A:
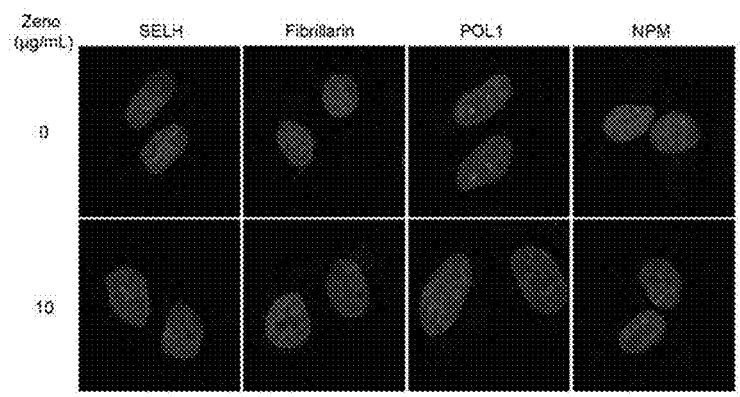
FIGS. 10A-10F are a combined photomicrographic, schematic and graphic presentation on ISP I's resulting in nucleolar stress response.
Figure 10B:
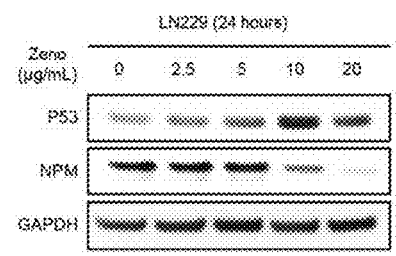
Figure 10C:
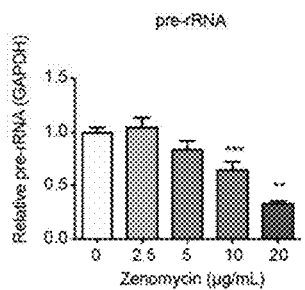
Figure 10D:
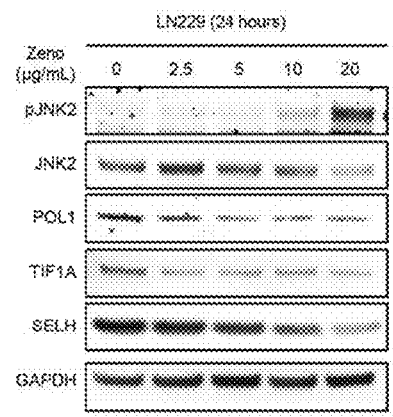
Figure 10E:
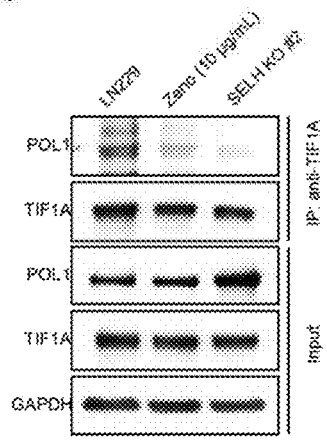
Figure 10F:
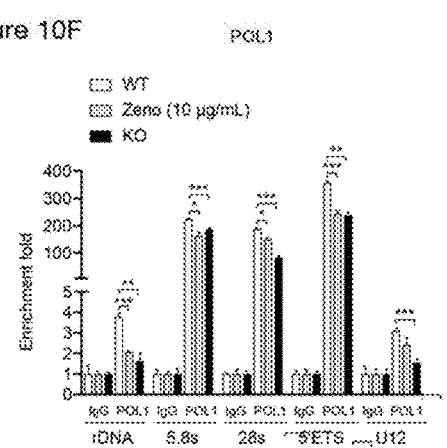

SELH is localized in the nucleolus, which is a sensor of oxidative stress. Yang et al., Nature communications 7: 13599 (2016); Novoselov et al., J. Biol. Chem. 282: 11960 (2007). Immunofluorescence staining showed a reduction of SELH expression in the nucleolus (FIG. 10A). ISP I treatment triggered the nucleolar stress response, including dispersion of nucleolar proteins (Neucleolin, Fibrillarin, POL1, NPM) detected by immunofluorescence (FIG. 10A), reduced NMP expression confirmed by western blot (FIG. 10B), and induction of the p53 pathway evaluated by western blot analysis of p53 (FIG. 10B). JNK2 activation by oxidative stress inactivated RNA polymerase I (POL1) transcription factor TIF1A in the nucleoli to down-regulate rRNA synthesis. Mayer et al., Genes Dev. 19: 933 (2005). To investigate whether the ribosomal biogenesis was disrupted by ISP I, pre-rRNA transcription was evaluated using real-time RT-PCR analysis in LN229 cells. ISP I reduced Pre-rRNA (PoL1 transcript) in a dose-dependent manner (FIG. 10C), evidencing decreased PoL1 transcription. To examine the mechanisms by which ISP I disrupts POL1 transcription, the inventors initially evaluated JNK2 activity and the overall state of the transcription machinery in ISP I-treated LN229 cells. Western blot demonstrated that JNK1 phosphorylation increased while the expression of POL1 and TIF1A slightly decreased in ISP I-treated cells (FIG. 10D). Co-immunoprecipitation assay demonstrated TIF1A physiologically interacted with POL1 in LN229 cells. Their interaction was disrupted by ISP I treatment or in SELH-deficient LN229 cells (FIG. 10E). As a chromatin immunoprecipitation (CHIP) assay revealed, moreover, ISP I treatment or a deficiency of SELH significantly reduced POL1 recruitment to the promoter coding regions of rDNA (FIG. 10F). These observations show that ISP I impairs POL1-rDNA interaction by activating the ROS/JNK2/TIF1A pathway.

ISP I Suppresses Tumorigenesis and Metastasis In Vivo

Figure 11A:
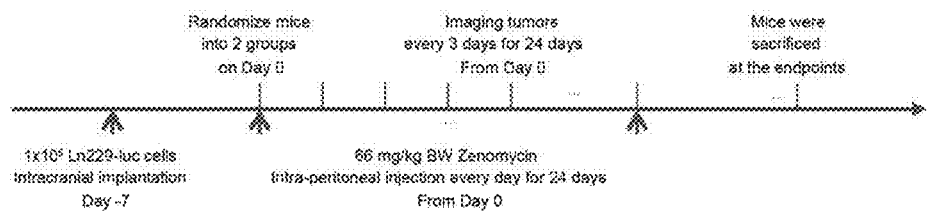
FIGS. 11A-11I are a combined schematic, graphic and photographic presentation of ISP I's suppression of tumor growth in glioblastoma xenograft mouse model and reduction of tumor burden in a melanoma lung metastasis mouse model.

To assess whether ISP I could suppress tumor growth in vivo, the inventors investigated the tumor-suppressing effect of ISP I in three xenograft mouse models (FIG. 11A and FIG. 12A, F).

Figure 11B:
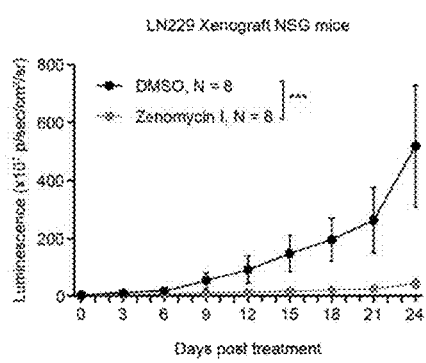
Figure 11C:
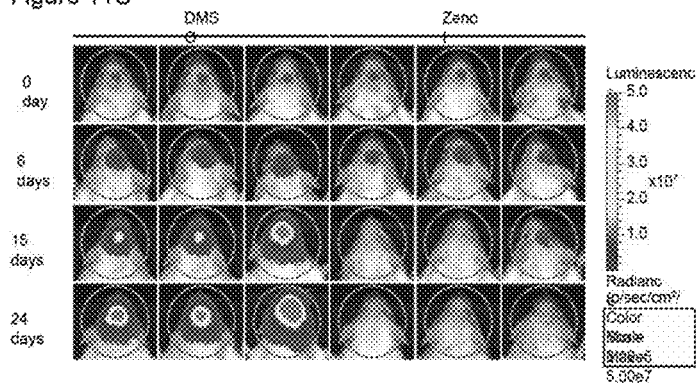

The inventors first assessed ISP I's anti-tumor activity in an intracranial mouse model (FIG. 11A). NSG mice were inoculated with $1 \times 10^5$ LN229-luc cells in the right-frontal cortex. After 7 days, intracranial tumor growth was confirmed via noninvasive in vivo bioluminescence imaging and mice were randomized into ISP I or DMSO (control) treatment groups. Bioluminescence imaging results demonstrated that mice treated with ISP I demonstrated significantly reduced tumor growth when compared to mice in the DMSO treatment group (FIG. 11B, C).

Figure 13A:
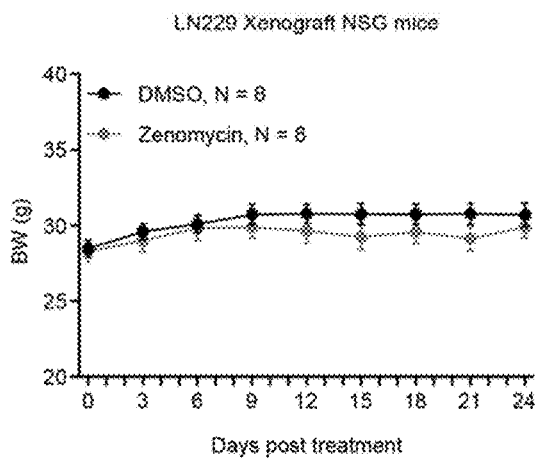
FIGS. 13A-13C present a series of line graphs of data evidencing that ISP I treatment was well-tolerated, with bodyweight maintenance by the experimental animals during treatment, in an LN229 xenograft NSG mouse model (FIG. 13A), a 786-O xenograft NSG mouse model (FIG. 13B), and an IOMM xenograft nude mouse model (FIG. 13C).
Figure 13B:
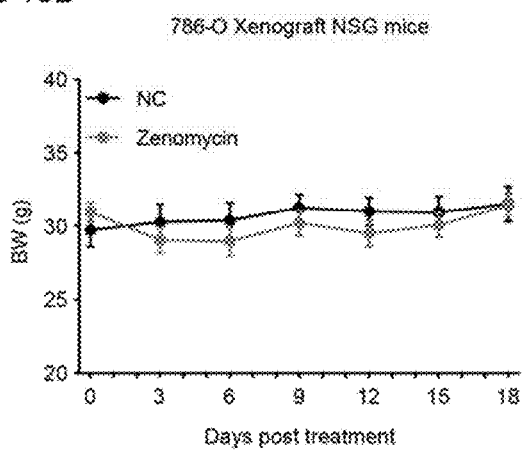
Figure 13C:
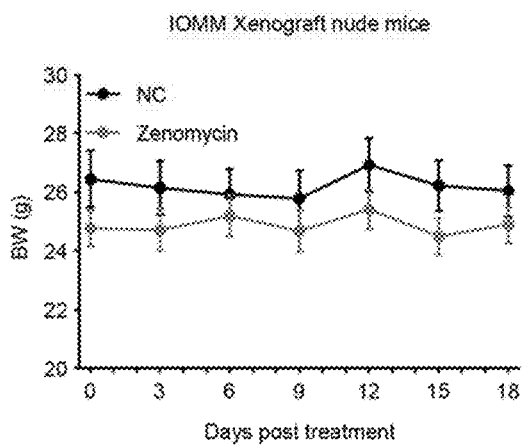

Since ISP I demonstrated a cytotoxic effect on RCC (FIG. 4) and meningioma cell lines (IOMM, JEN, CH-157) (FIG. 12D, E), the inventors also assessed whether ISP I reduced tumor growth in 786-O (FIG. 12A-C) and IOMM (FIG. 12F-H) xenograft models. In both models, ISP I-treated mice demonstrated significantly reduced tumor size and weight compared to DMSO-treated groups (FIG. 12C, H). In all models, ISP I treatment was well-tolerated, and animals maintained their bodyweight (FIG. 13A-C). A dedicated veterinary histopathology review of major organs and standard clinical chemistry undertaken 24 days after treatment revealed no hematologic, renal, pancreatic or liver toxicities.

Figure 11D:
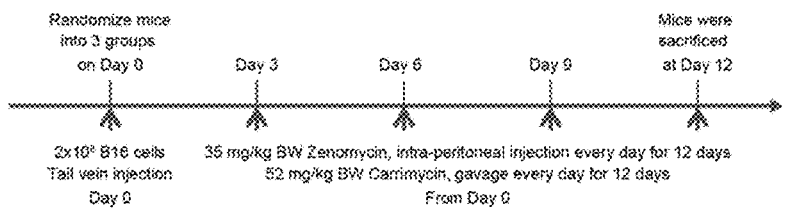

In addition to the aforementioned xenograft tumor models, the anti-tumor activity of ISP I was assessed in a metastatic murine melanoma (B16) model. Mice were intravenously injected with $2 \times 10^5$ B16 cells and randomized into the following three treatment groups: ISP I (35 mg/kg), Carrimycin (56 mg/kg), Saline (control) (FIG. 11D). After 12 days of treatment, mice in the ISP I and Carrimycin treatment groups demonstrated significantly reduced lung tumor nodules when compared to saline treated mice (FIG. 11E, F). These data evidence that both ISP I and Carrimycin inhibit the formation of metastatic melanoma tumors.

Figure 11G:
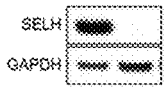
Figure 11H:
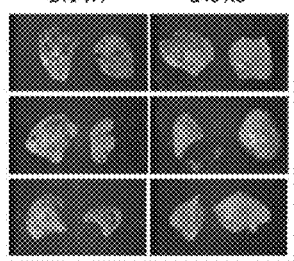
Figure 11E:
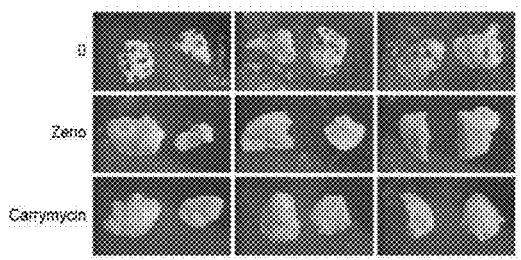
Figure 11F:
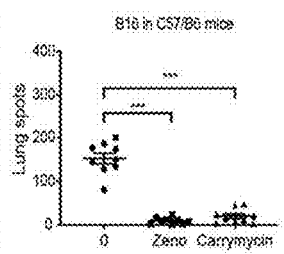
Figure 11I:
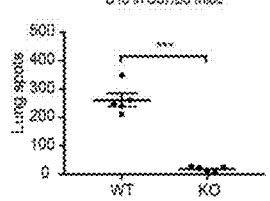

To evaluate SELH's role in metastatic melanoma tumor formation, the inventors inoculated C57/B6 mice with SELH-deficient B16 cells or B16-wild-type cells (FIG. 11G). Twelve days after tumor inoculation, mice injected with SELH-deficiency B16 cells demonstrated significantly reduced lung tumor nodules when compared to mice injected with B16-wild-type cells (FIG. 11H, I). Taken together, these in vivo data indicate that ISP I induces a potent anti-tumor effect through the inhibition of SELH activity.

Methods

Cell Culture and Reagents

Glioblastoma cell lines (LN229, U118, T98G and A172) were derived from American Type Culture Collection (ATCC) of Manassas, Va. U251 was obtained from Sigma Aldrich (St. Louis, Mo.). LN229-luc cells were generated by stable transfection of luciferase-containing lentivirus (EF1a-ffLuc2-eGFP) into naïve U251 cells. Twenty-four hours later, the transfected cells were subjected to puromycin (Sigma) at 1 µg/mL for 7 days. One week after selection, the surviving clones were expanded and followed by extraction of total protein for standard western blotting analysis.

U2OS cells obtained from ATCC were transfected with plasmid containing RNaseH1 construct mutated at D210N (Addgene #111904) and WKKD (Addgene #111905). Stable monoclonal cells were selected with hygromycin.

Renal cell carcinoma cell lines ACHN and 786-O were obtained from ATCC. UM-RC-2 cells were purchased from Sigma, while RCC4 was a gift from Eric Jonasch (MD Anderson). B16-F10 cells were purchased from ATCC. All cells were cultured in Dulbecco's Modified Eagle Medium (DMEM; Gibco) supplemented with 10% fetal bovine serum (FBS; Gibco) and 1% penicillin and streptomycin (Gibco). Small interfering RNA (siRNA) targeting SELH (IDT) were transfected into cells for 48 hours using Lipofectamine RNAiMAX reagent (Invitrogen).

SELH knockout LN229 cell lines and B16 were generated using the CRISPR/Cas9 technique described by Shalem et al., *Science* 343: 84 (2014). The gDNA for targeting SELH was designed as follows: Oligo 1, 5'-GCCTTACGCTTCCTCCCGCG-3'; Oligo 2, 5'-CTCGGCTACGGCGACCACCG-3'; the gDNA for targeting mouse SELH was designed as follows: Oligo 1, 5'-GTAAGGCGGGGGCCGCGCCTA-3'; Oligo 2, 5'-GCGCCTTACGCTTTCTTCCGT-3', and subcloned into Cas9 carrying vector (pX330). The two resultant plasmids and puromycin-expressing vector (pPGK-puro) were co-transfected at a ratio of 1:1:1 into LN229 or B16 cells using Lipofectamine 2000 (Invitrogen). Twenty-four hours later, the transfected cells were subjected to puromycin (Sigma) at 1 µg/mL for 7 days. One week after selection, the surviving clones were expanded, followed by extraction of total protein for standard western blotting analysis.

Real-Time PCR

Total RNA was extracted using PureLink RNA Mini Kit, a product of ThermoFisher Scientific (Waltham, Mass. USA), according manufacturer's protocol. First strand cDNA was synthesized with iScript cDNA Synthesis Kit, a product of Bio-Rad (Hercules, Calif. USA). Then the inventors performed real time PCR by SsoAdvanced Universal SYBR Green Supermix kit, a product of Bio-Rad, to quantify the expression levels of genes NRF2, HMOX1, and NQO1. The primer sequences are described in Liu et al., *J. Nat'l Cancer Inst.* 111: 1033 (2019). Data were analyzed and normalized to 18s rRNA as the reference gene for further statistics.

Immunoblotting

Western blotting was performed to detect the protein expression level of SELH, NRF2 and γH2AX regulated by ISP I. The cells were lysed by RIPA buffer from ThermoFisher Scientific, and the concentration was measured using DC Protein Assay, a Bio-Rad product. Equal amounts of protein of each sample were loaded for gel electrophoresis and were transferred to nitrocellulose membrane, blocked and incubated overnight at 4° C. with primary antibodies. Then the membranes were washed with TBST (3 times, 10 min each). Exposure, imaging, and data analysis were done using a KwikQuant Imager system, a product of Kindle Biosciences (Greenwich, Conn. USA). The following antibodies were used: anti-phospho-histone H2A.X (Ser139), anti-NRF2 (Cell Signaling, Danvers, Mass. USA), anti-SELH (Abcam, Cambridge, Mass. USA), anti-GAPDH (Millipore, Temecula, Calif. USA).

Immunohistochemistry

For immunofluorescence assay, cells were seeded on a 35-mm confocal dish with glass bottom and were treated with ISP I. After 24 hours, cells were fixed with 4% paraformaldehyde and were labeled with primary antibodies against γH2AX overnight at 4° C. Then the cells were incubated with secondary antibody conjugated with Alexa Fluor-594 (Invitrogen), followed by staining with DAPI for nuclei. Images were obtained using Zeiss LSM 780 microscopy (Carl Zeiss, Oberkochen Germany).

EdU and R-loop staining for U2OS cells was conducted as follows: U2OS cells were incubated with EdU for 20 min and washed with a brief PBS wash. These cells were then pre-extracted in PBS-T buffer (0.2% Triton X-100 in 1×PBS, phenylmethylsulphonylfluoride [PMSF], protease inhibitor cocktail (Sigma, P8340) and phosphatase inhibitor cocktail (Roche, P4906845001)) for 3 min on ice and washed with a brief PBS wash. Pre-extracted cells were fixed using 2.0% paraformaldehyde (PFA) solution in PBS. EdU staining was performed according to the manufacturer's instructions. Primary antibody staining was performed as follows: anti-V5-tag (Santacruz, sc-271926, 1:250 dilution). Secondary antibody staining was performed as follows: Alexa 568 conjugated anti-mouse IgG (1:500, ThermoFisher Scientific). A Zeiss LSM710 confocal microscopy was used for imaging. Images where scored in ZenBlue software by counting non-nucleolar R-loops foci, where nucleoli were masked based on intensity and size of R-loop staining and number of foci counted in the rest of the nucleus.

Cell Viability Assay

Cell viability was measured by Cell Counting Kit-8 (CCK-8, Dojindo Molecular Technologies, Tokyo, Japan). Cells were seeded in 96-well plates at a density of $3\times10^3$ cells/well and cultured for 24 hours before treatment with ISP I at different concentration. After treatment for a gradient ISP I concentration from 0 to 20 µg/ml for 48 hours, while control groups were only treated in PBS solution, 10 µl of CCK-8 solution were added to each well and cells were incubated for an additional 2 hours. The absorbance in each well at a wavelength of OD450 was detected by the Synergy H1 microplate reader, a product of BioTek (Winooski, Vt. USA).

Cell Apoptosis and Cell Cycle

Cells ($2\times10^5$) were plated in 6-well plates and treated with different concentrations of ISP I. Then the cells were harvested and washed three times with PBS. Cells were resuspended in 100 µl binding buffer and were incubated with 5 µl APC-conjugated Annexin V working solution, a product of BD bioscience (Franklin Lakes, N.J. USA), and 1 µl propidium iodide (PI), a product of Invitrogen, for 15 min at room temperature with protection from light. Data acquisition and quantification were processed with BD LSR-Fortessa flow cytometer, using FlowJo software (Ashland, Oreg. USA).

For monitoring cell-cycle arrest of ISP I-treated cells, Click-iT EdU Flow Cytometry Assay Kits were used, a product of ThermoFisher Scientific. Cells were co-cultured with EdU at a concentration of 10 µM for 1 hour. After fixation and permeabilization, EdU-positive cells were labeled with Alexa Fluor 647 fluorescein. DAPI also was used for measuring total DNA content to identify differences in cell cycle phases. Data were collected by means of a BD LSRFortessa flow cytometer using FlowJo software. Cells that are positive with EdU and DAPI were in S-Phase of the cell cycle.

Analysis of Mitochondria Superoxide

To detect changes in mitochondrial superoxide after treatment with ISP I, the inventors used the MitoSOX Red mitochondrial superoxide indicator kit, a product of ThermoFisher Scientific. MitoSOX Red exhibited red fluorescence to indicate specifically the superoxide generated in the mitochondria. Cells were incubated with 5 µM MitoSOX Red for 15 min at room temperature, followed by flow cytometry analysis. Excitation by means of a 561 nm laser and a 610/20 discriminating filter was applied by a BD LSRFortessa flow cytometer.

Cell ROS and Glutathione-Dependent Peroxidases Levels Measurement

Cell ROS level change brought about by ISP I was measured by ROS-Glo H2O2 assay kit, a product of Promega (Madison, Wis. USA). After treatment with ISP I for 24 hours, $H_2O_2$ substrate was added and cells were incubated for 6 hours. After incubation the supernatant was collected and was incubated with ROS-Glo™ Detection Solution for 20 min at room temperature with protection from light. Luciferase data were obtained with the Synergy H1 microplate reader, a product of BioTek (Winooski, Vt. USA).

Glutathione peroxidase kit (Abcam, Cambridge, Mass. USA) was used to quantitate the activity of all of the glutathione-dependent peroxidases in live cells ($2\times10^6$), which were harvested and homogenized with assay buffer provided in the kit. Then the supernatant was collected and incubated in accordance with the manufacturer's instructions. Absorbance at 340 nm was measured using the microplate reader mentioned above.

Drug Affinity Responsive Target Stability (DARTS) Assay

DARTS assay data were taken to identify the target of ISP I in vitro. For this assay, the invenots used the protocol published by Lomenick et al., *Proc. Nat'l Acad. Sci. USA* 106: 21984 (2009). Briefly, LN229 cells were lysed with M-PER (Pierce) supplemented with protease and phosphatase inhibitors. After centrifugation at 14,000 rpm for 15 min, lysates were diluted to the same final volume and protein concentration with M-PER and were dissolved in TNC buffer [50 mM Tris-HCl (pH 8.0), 50 mM NaCl, 10 mM $CaCl_2$)]. All steps were performed on ice or at 4° C. to help prevent premature protein degradation. After incubation of the protein sample with ISP I (40 µg/mL) or DMSO as a control at room temperature for one hour, each sample then was proteolyzed with 2 µL 1:100 Pronase at room temperature for 30 min. To stop proteolysis, 3 µL cold 20× Protease inhibitor were added to each sample, mixed well, and placed on ice. The digested peptide was filtered through a Vivacon 500 10K spin column, was precipitated using acetone, and then was digested with trypsin as previously described. Peptides were analyzed by LC/MS/MS on a Thermo LTQ-Orbitrap mass spectrometer with an Eksigent LC pump. For quantitative comparison of protein and peptide abundances, MS spectra were analyzed by means of the differential workflow of Rosetta Elucidator (Rosetta Inpharmatics).

Cellular Thermal Shift Assay (CETSA)

CETSA experiments were performed to determine the ISP I-related ligand induced shifts. Intact and live cells in a 10-cm dish were harvested, washed and resuspended in PBS with protease inhibitor cocktail. Protein of the cells was extracted by freeze-thaw more than three times, using liquid nitrogen. The supernatant was centrifuged at 20,000 g for 20 min at 4° C. Then the samples were aliquoted to several groups incubated with different concentrations of ISP I for 1 hour. After that, samples were aliquoted into PCR tubes and thereafter heated at gradient temperature ranging from 40° C. to 80° C. for 3 min. Then the samples were centrifuged again and resolved using 4-12% SDS-PAGE followed by western blot experiments.

Surface Plasmon Resonance (SPR) Assay

The affinities constant (KD) and kinetics (ka and kd) of ISP I binding to SELH (Sec44→Cys44) were assayed using Biacore 8K (GE Healthcare, Sweden), all at 25° C. The stock solution 10×PBS-P+ (with 0.5% P20), provided by GE, was used to prepare running buffers, 4-point solvent correction and samples for binding in 5% DMSO. The purified active SELH (Sec44→Cys44) was diluted by 10 mM sodium acetate solution at pH 5.5, resulting in a protein concentration of 50 μg/mL. Coupling conditions were determined by protein isoelectric points. The diluted protein was immobilized on the surface of a CM5 sensor chip via the primary amine group, employing a standard Amine Coupling Kit, and the target immobilization level was 7000 response units (RUs).

To determine the binding affinity between ISP I and SELH (Sec44→Cys44), a series of ISP I dilutions was analyzed by single-cycle kinetics. As the analyte, a concentration gradient of ISP I was freshly prepared in PBS-P+ running buffer (with 5% DMSO), with at least five concentrations (31.25, 62.5, 125, 250, 500 μm). The ISP I at various gradient concentrations and one zero concentration (running buffer) flowed over the immobilized SELH, with 120 s for binding, followed by disassociation for 120 s, and the obtained response units (RUs) were recorded. The RU values were collected, and the binding affinity data were calculated by kinetic models (1:1 interaction) within Biacore 8K Evaluation Software. The equilibrium dissociation constant (KD) was calculated to evaluate the ability of ISP I to interact with SELH.

Co-Immunoprecipitation

For co-immunoprecipitation analysis, LN229 wild-type cells, LN229 cells treated with 10 μg/mL of ISP I, and LN229 cells transfected with SELH siRNA for 24 hours were harvested, and total protein was prepared from cells using Dynabeads Co-Immunoprecipitation Kit (ThermoFisher) according to the manufacturer's protocol. Immunoblotting then was performed using anti-SELH antibody.

ChIP Assay

ChIP assays were performed using a SimpleCHIP Enzymatic Chromatin IP Kit (Magnetic beads) following the manufacturer's instructions (Cell Signaling Technology; catalog 9003). Cross-linked protein-DNA complexes were precipitated by incubating with rabbit anti-POL1A (CST; 24799s) or rabbit IgG (negative control) overnight and then with magnetic beads for 2 hours. Purified DNA fragments, including HIF2a and ER-binding elements, were analyzed quantitatively by real-time PCR with primers against the rDNA promoter and gene body, following the standard-curve method. The standard curves were created by serial dilution of 2% input chromatin DNA. The values of chromatin DNA precipitated by POL1 antibody were normalized to those precipitated by normal rabbit IgG, which is arbitrarily defined as 1. The primer sequences are described by Frankowski et al., Science translational medicine 10: eaap8370 (2018).

Xenograft and Lung Melanoma Metastasis Mouse Model

Mice experiments were approved by the National Institute of Neurological Disorders and Stroke (NINDS) and National Cancer Institute (NCI) Animal Use and Care Committees. For intracranial xenografts establishment, NOD-Prkdc$^{scid}$Il2rg$^{tmiWjl}$ (NSG) mice (6-8 weeks old from the NCI-Frederick animal facility) were inoculated intracranially with 100,000 LN229-luc cells suspended in 2 μL Hank's Balanced Salt Solution (HBSS), a product of Crystalgen (Commack, N.Y. USA). After one week, luciferin signals were detected to confirm the survival of tumor cells in mice. The mice were assigned to the indicated groups according to the signal intensity, in order to keep the baseline balanced. ISP I was injected intraperitoneally daily at a dose of 66 mg/kg body weight for 24 days. The mice in control group were injected with the same volume of corn oil or saline. The viability of tumors was monitored every four days. Survival end point for all animal studies was defined as when any of the following criteria were reached: 1) a loss of more than 15% of body weight, 2) protruded skull, 3) head tile, 4) hunched posture, 5) ataxia, 6) rough hair coat, or 7) impaired mobility.

For subcutaneous xenografts, NSG mice (6-8 weeks old) from the NCI-Frederick animal facility and Jackson Lab (Bar Harbor, Me. USA) were injected with $5 \times 10^6$ to $1 \times 10^7$ cells subcutaneously in the flank. One week later, the tumor-bearing mice were randomly assigned to different groups and made the tumor volume baseline equivalent and treated with normal saline or Zenomycin (35 mg/kg) everyday intraperitoneally. Tumors were measured using a caliper, and volume was calculated.

For metastasis study, C57BL/6 mice (4-5 weeks) from Charles River Laboratories (Wilmington, Mass. USA) were assigned randomly to one or another of two groups, 9 animals per group. B16-F10 mouse skin melanoma cells ($2 \times 10^5$) were resuspended in 100 μl saline and injected through tail vein. After treatment with ISP I at 35 mg/kg for 12 days, all mice were euthanized, and the lungs were examined for counting black metastasis dots.

Statistics

Data were presented as the mean and standard deviation (SD) or standard error of the mean (SEM), as indicated. Other variables were analyzed using two-way ANOVA or unpaired Student's t-test, as appropriate. Statistical analyses were performed using GraphPad Prism 6, a product of GraphPad Software (San Diego, Calif. USA). A $p<0.05$ was considered as statistically significant.

The present invention has been disclosed with reference to embodiments that are illustrative, not limiting. From reading this description, those of skill in the art may appreciate changes and modifications that may be made that do not depart from the scope and spirit of the invention as described above and claimed hereafter.

What is claimed is:

1. A method for inhibiting metastasis, comprising prophylactically administering to a subject who has a cancerous condition a medicament comprising (A) a compound selected from the group consisting of isovalerylspiramycin I, isovalerylspiramycin II and isovalerylspiramycin III or (B) a mixture comprising any two or more thereof, wherein said medicament is administered in a therapeutically effective amount to inhibit metastasis in said subject,
   wherein said administering begins before or after a cancer treatment and is chronic over a period of three months or more.

2. The method according to claim 1, wherein said administering begins before the cancer treatment.

3. The method according to claim 1, wherein said administering begins after the cancer treatment.

4. The method according to claim 1, wherein said administering begins before and continues after the cancer treatment.

5. The method according to claim 1, wherein said medicament comprises a compound selected from the group consisting of isovalerylspiramycin I, isovalerylspiramycin II and isovalerylspiramycin III.

6. The method according to claim 5, wherein said medicament comprises isovalerylspiramycin I.

7. The method according to claim 1, comprising administering to said subject a mixture of any two or more of isovalerylspiramycin I, isovalerylspiramycin II and isovalerylspiramycin III.

8. The method according to claim 7, wherein said mixture is Carrimycin.

9. The method according to claim 1, wherein said cancerous condition is characterized by nucleolar hypertrophy.

10. The method according to claim 1, wherein said subject is an end-stage cancer patient.

11. The method according to claim 1, wherein said cancerous condition is selected from the group consisting of melanoma, liver cancer, pancreatic cancer, blood cancer, brain cancer, breast cancer and colon cancer.

12. The method according to claim 1, wherein said cancerous condition is selected from the group consisting of diffuse large B-cell lymphoma, acute myeloid leukemia, pancreatic adenocarcinoma, thyroid carcinoma, thymoma, uterine corpus endometrial carcinoma, uterine carcinosarcoma and uveal melanoma.

13. The method according to claim 1, wherein said cancerous condition involves a tumor deficient for DNA damage repair.

14. The method according to claim 1, wherein said cancerous condition involves a cancer that displays accelerated rRNA synthesis.

15. The method according to claim 1, wherein said administering is chronic over a period of six months or more.

16. The method according to claim 1, wherein said administering is chronic over remainder of the subject's life.

17. The method according to claim 1, wherein said therapeutically effective amount is not more than about 8 milligrams per kilogram of human body weight per day.

* * * * *